US009365862B1

(12) United States Patent
Dweikat

(10) Patent No.: US 9,365,862 B1
(45) Date of Patent: Jun. 14, 2016

(54) HERBICIDE RESISTANT SORGHUM MUTANTS

(75) Inventor: Ismail M. Dweikat, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 712 days.

(21) Appl. No.: 13/480,576

(22) Filed: May 25, 2012

Related U.S. Application Data

(60) Provisional application No. 61/490,114, filed on May 26, 2011.

(51) Int. Cl.
*A01H 5/10* (2006.01)
*C12N 15/82* (2006.01)
*A01H 1/02* (2006.01)

(52) U.S. Cl.
CPC .............. *C12N 15/8274* (2013.01); *A01H 5/10* (2013.01)

(58) Field of Classification Search
CPC .............................. A01H 5/10; C12N 15/8274
See application file for complete search history.

(56) References Cited

U.S. PATENT DOCUMENTS

| 4,940,838 | A | | 7/1990 | Schilperoort et al. |
| 4,945,050 | A | | 7/1990 | Sanford et al. |
| 5,057,422 | A | | 10/1991 | Bol et al. |
| 5,187,267 | A | | 2/1993 | Comai et al. |
| 5,501,967 | A | | 3/1996 | Offringa et al. |
| 5,824,877 | A | | 10/1998 | Hinchee et al. |
| 5,853,973 | A | * | 12/1998 | Kakefuda ........... C12N 15/8278 435/232 |
| 5,981,839 | A | | 11/1999 | Knauf et al. |
| 5,981,840 | A | | 11/1999 | Zhao et al. |
| 6,051,757 | A | | 4/2000 | Barton et al. |
| 6,369,298 | B1 | | 4/2002 | Cai et al. |
| 6,395,684 | B1 | | 5/2002 | Feucht et al. |
| 6,403,535 | B1 | | 6/2002 | Muller et al. |
| 2008/0216187 | A1 | * | 9/2008 | Tuinstra ............. C12N 15/8278 800/260 |
| 2010/0287641 | A1 | * | 11/2010 | McElver ................. C12N 9/88 800/260 |

FOREIGN PATENT DOCUMENTS

EP 0 292 435 11/1988

OTHER PUBLICATIONS

Tranel, Patrick J., and Terry R. Wright. "Resistance of weeds to ALS-inhibiting herbicides: what have we learned?." 2002.*
Anderson et al., "Discovery of a Primisulfuron-Resistant Shattercane (*Sorghum bicolar*) Biotype," *Weed Tech.*, 1998, 12:74-77.
Anderson et al., "Mechanism of primisulfuron resistance in a shattercane (*Sorghum bicolor*) biotype," *Weed Sci.*, 1998, 46:158-162.
Ballas et al., "Efficient functioning of plant promoters and poly(A) sites in Xenopus oocytes," *Nucleic Acids Res.*, 1989, 17:7891-7903.
Bevan et al., "A chimaeric antibiotic resistance gene as a selectable marker for plant cell transformation," *Nature*, 1983, 304:184.
Blochlinger & Diggelmann, "Hygromycin B phosphotransferase as a selectable marker for DNA transfer experiments with higher eucaryotic cells," *Mol. Cell. Biol.*, 1984, 4:2929.
Bourouis et al., "Vectors containing a prokaryotic dihydrofolate reductase gene transform *Drosophila* cells to methotrexate-resistance," *EMBO J.*, 1983, 2:1099-1104.
Casas et al., "Transgenic sorghum plants via microprojectile bombardment," *Proc. Natl. Acad. Sci. USA*, 1993, 90:11212-11216.
Chaleff and Mauvais, "Acetolactate Synthase Is the Site of Action of Two Sulfonylurea Herbicides in Higher Plants," *Science*, 1984, 224:1443-1445.
Chao et al., "Leucine aminopeptidase RNAs, proteins and activities increase in response to water deficit, salinity and the wound signals: systemin, methyl jasmonate, and abscisic acid," *Plant Physiol.*, 1999, 120:979-992.
Christopher et al., "Cross-Resistance to Herbicides in Annual Ryegrass (*Lolium rigidum*)," *Plant Physiol.*, 1991, 95:1036-1043
Christopher et al., "Resistance to Acetolactate Synthase-Inhibiting Herbicides in Annual Ryegrass (*Lolium rigidum*) Involves at Least Two Mechanisms," *Plant Physiol.*, 1992, 100:1909-1913.
Corbett et al., "Detection of resistance to acetolactate synthase inhibitors in weeds with emphasis on DNA-based techniques: a review," *Pest Manag. Sci.*, 2006, 62:584-597.
Crossway et al., "Micromanipulation techniques in plant biotechnology," *BioTechniques*, 1986, 4:320-334.
DeBlock et al., "Expression of foreign genes in regenerated plants and in their progeny," EMBO J., 1984, 3:1681-1689.
Durner et al., "Oligomeric Forms of Plant Acetolactate Synthase Depend on Flavin Adenine Dinucleotide," Plant Physiol., 1990, 93:1027-1031.
Fang et al., "Sequence of two acetohydroxyacid synthase genes from *Zea mays*," *Plant Mol. Biol.*, 1992, 18:1185-1187.
Fraley et al., "Expression of bacterial genes in plant cells," *Proc. Natl. Acad. Sci, USA*, 1983, 80:4803-4807.
Fraley et al., "Liposome-mediated delivery of tobacco mosaic virus RNA into tobacco protoplasts: A sensitive assay for monitoring liposome-protoplast interactions," *Proc. Natl. Acad. Sci. USA*, 1982, 79:1859-1863.
Fromm et al., "Expression of genes transferred into monocot and dicot plant cells by electroporation," *Proc. Natl. Acad. Sci. USA*, 1985, 82:5824-5828.
Gerwick et al., "Mechanism of action of the 1,2,4-triazolo[1,5-a] pyrimidines," *Pestic. Sci.*, 1990, 29:357-364.
Guerineau et al., "Effect of deletions in the cauliflower mosaic virus polyadenylation sequence on the choice of the polyadenylation sites in tobacco protoplasts," *Mol. Gen. Genet.*, 1991, 262:141-144.

(Continued)

*Primary Examiner* — Russell Kallis
*Assistant Examiner* — Weihua Fan
(74) *Attorney, Agent, or Firm* — Fish & Richardson P.C.

(57) ABSTRACT

This disclosure provides for four different sorghum mutants that exhibit resistance to ALS-inhibiting herbicides. This disclosure also provides for methods of using such sorghum mutants that exhibit resistance to ALS-inhibiting herbicides in breeding methods to make sorghum hybrids, varieties, or lines. The sorghum hybrids, varieties, and lines provided in this disclosure can be used in methods of controlling weeds.

7 Claims, No Drawings

(56) References Cited

OTHER PUBLICATIONS

Hayashimoto et al., "A Polyethylene Glycol-Mediated Protoplast Transformation System for Production of Fertile Transgenic Rice Plants," *Plant Physiol.*, 1990, 93:857-863.

Herrera-Estrella, "Expression of chimaeric genes transferred into plant cells using a Ti-plasmid-derived vector," *Nature*, 1983, 303:209-213.

Horsch et al., "Inheritance of functional foreign genes in plants," *Science*, 1984, 223:496-498.

Kalderon et al., "A short amino acid sequence able to specify nuclear location," *Cell*, 1984, 39:499-509.

Krens et al., "In vitro transformation of plant protoplasts with Ti-plasmid DNA," *Nature*, 1982, 296:72-74.

Lassner et al., "Targeting of T7 RNA polymerase to tobacco nuclei mediated by an SV40 nuclear location signal," *Plant Mol. Biol.*, 1991, 17:229-234.

Lee et al., "Comparison of ALS inhibitor resistance and allelic interactions in shattercane accessions," *Weed Sci.*, 1999, 47:275-281.

Menendez et al., "Detoxification of chlorotoluron in a chlorotoluron-resistant biotype of Alopecurus myosuroides. Comparison between cell cultures and whole plants," *Physiologia Plantarum*, 1997, 99:97-104.

Mogen et al., "Upstream Sequences Other than AAUAAA Are Required for Efficient Messenger RNA 3'—End Formation in Plants," *Plant Cell*, 1990, 2:1261-1272.

Munroe et al., "Tales of poly(A): a review," *Gene*, 1990, 91:151-158.

Odell et al., "Identification of DNA sequences required for activity of the cauliflower mosaic virus 35S promoter," *Nature*, 1985, 313:810.

Paszkowski et al., "Direct gene transfer to plants," *EMBO J.*, 1984, 3:2717.

Proudfoot, "Poly(A) signals," *Cell*, 1991, 64:671-674.

Riggs et al., "Stable transformation of tobacco by electroporation: evidence for plasmid concatenation," *Proc. Natl. Acad. Sci. USA*, 1986, 83:5602.

Rosenberg et al., "Vectors for selective expression of cloned DNAs by T7 RNA polymerase," *Gene*, 1987, 56:125-135.

Saari et al., 1994, "Resistance to acetolactatesynthase inhibiting herbicides," pp. 83-139, Eds. Powles and Holtum, Herbicide Resistance in Plants: Biology and Biochemistry, CRC, Boca Raton, FL.

Sanfacon et al., "A dissection of the cauliflower mosaic virus polyadenylation signal," *Genes Dev.*, 1990, 5:141-149.

Shaner et al., Imidazolinones Potent inhibitors of acetohydroxyacid synthase, *Plant Physiol.*, 1984, 76:545-546.

Shaner, "Resistance to Acetolactate Synthase(ALS) Inhibitors in the United States: History, Occurrence, Detection, and Management," *Weed Sci.*, 1999, 44:405-411.

Spencer et al., "Bialaphos selection of stable transformants from maize cell culture," *Theor. Appl. Genet.*, 1990, 79:625

Stidham, "Herbicides that Inhibit Acetohydroxyacid Synthasel," *Weed Sci.*, 1991, 39:428-434.

Veldhuis et al., "Metabolism-based resistance of a wild mustard (*Sinapis arvensis* L.) biotype to ethametsulfuron-methyl," *J. Agric. Food Chem.*, 2000, 48:2986-90.

Vieira and Messing, "The pUC plasmids, an M13mp7-derived system for insertion mutagenesis and sequencing with synthetic universal primers," *Gene*, 1982, 19: 259-268.

White et al., "A cassette containing the bar gene of Streptomyces hygroscopicus: a selectable marker for plant transformation," *Nucl Acids Res.*, 1990, 18:1062.

\* cited by examiner

SEQUENCE LISTING

<160> NUMBER OF SEQ ID NOS: 22

<210> SEQ ID NO 1
<211> LENGTH: 2228
<212> TYPE: DNA
<213> ORGANISM: Sorghum bicolor subsp. X drummondii

<400> SEQUENCE: 1

```
caccatggcc accaccgccg ccgccgccgc cgccgcgcta gccgccgcca ctaccgctgc      60
gcccaaggcg aggcgccggg cgcacctcct ggccgcacgg cgcgccctcg ccgcgcccat     120
caggtgctca gcggcgccac ccgccacgct gacggtgacg gctcccccgg ccaccccgct     180
ccggccgtgg ggccccaccg atccccgcaa gggcgccgac atcctcgtcg aggctcttga     240
gcgctgcggc gtccgcgacg tcttcgccta ccccggcggc gcgtccatgg agatccacca     300
ggcactcacc cgttcccccg tcatcgccaa ccacctcttc cgccacgagc aaggggaggc     360
cttcgccgcc tctggcttcg cgcgctcctc gggccgcgtc ggcgtctgcg tcgccacctc     420
cggccccggc gccaccaacc tagtctccgc gctcgccgac gcgctgctcg actccgtccc     480
catggtcgcc atcacgggac aggttccgcg gcgcatgatt ggcaccgacg ccttccagga     540
gacgcccatc gtcgaggtca cccgctccat caccaaacat aactacctgg tcctcgacgt     600
cgacgacatc ccccgcgtcg tgcaggaggc tttcttcctc gcctcctccg gtcgcccggg     660
accggtgctt gtcgacatcc ccaaggacat ccagcagcag atggccgtgc cggtctggga     720
cacgcccatg agtctgcctg ggtacattgc gcgccttccc aagcctcctg cgactgaatt     780
gcttgagcag gtgctgcgtc ttgttggtga atcaaggcgc cctgttcttt atgttggtgg     840
tggctgcgca gcatctggcg aggagttgcg ccgctttgtg gagatgactg gaatcccagt     900
cacaaccact cttatgggcc ttggcaattt ccctggcgac gacccactgt ctctgcgcat     960
gcttggtatg catggcacgg tgtatgcaaa ttatgcagtg gataaggcgg atctgttgct    1020
tgcatttggt gtgcggtttg atgatcgtgt gacagggaag attgaggctt ttgcaagcag    1080
ggctaagatt gtgcacattg atattgatcc cgctgagatt ggcaagaaca agcagccaca    1140
tgtgtccatc tgtgcagacg ttaagcttgc tttgcagggc atgaatgctc ttctggaagg    1200
aagcacatca aagaagagct ttgactttgg ctcatggcaa gctgagttgg atcagcagaa    1260
gagagagttc ccccttgggt ataaaactttt tgatgacgag atccagccac aatatgctat    1320
tcaggttctt gatgagctga caaaggggaa ggccatcatt gccacaggtg ttgggcagca    1380
ccagatgtgg gcggcacagt actacactta caagcggcca aggcagtggt tgtcttcagc    1440
tggtcttggg gctatgggat ttggtttgcc ggctgctgct ggcgctgctg tggccaaccc    1500
aggtatcact gttgttgaca tcgacggaga tggtagcttc ctcatgaaca ttcaggagct    1560
agctatgatc cgaattgaga acctcccagt gaagatcttt gtgctaaaca accagcacct    1620
ggggatggtg gtgcagtggg aggacaggtt ctataaggcc aacagagcgc acacatactt    1680
gggaaaccca gagaatgaaa gtgagatata tccagatttc gtgacaattg ccaaagggtt    1740
caacattcca gcagtccgtg tgacaaagaa gagcgaagtc catgcagcaa tcaagaagat    1800
gcttgagact ccagggccat acctcttgga tataatcgtc ccgcaccagg agcatgtgtt    1860
```

-continued

```
gcctatgatc cctagtggtg gggctttcaa ggatatgatc ctggatggtg atggcaggac    1920
tgtgtattga tctaaatttc agcatgcaca tctccctgcc tttctttgac atgcatatga    1980
gctggtacaa gggtgatgtg ttatttatgt gatgttctcc tgtgttctat cttttgtaa    2040 gccgtcagct atctatagtg tgcttgtttg atgtactctg ttatggtaat cttaagtagt    2100
ttcctacctt gtagtggtgt agtctgttgt ttcatgctgg catatctgtc atcagaggtc    2160
atgtaagtgc cttttgctac agataaaataa ggaaataagc attgctatgc agtggttctg    2220
tacgaagc                                                              2228
```

<210> SEQ ID NO 2
<211> LENGTH: 642
<212> TYPE: PRT
<213> ORGANISM: Sorghum bicolor subsp. X drummondii

<400> SEQUENCE: 2

```
Thr Met Ala Thr Thr Ala Ala Ala Ala Ala Ala Leu Ala Ala Ala
 1               5                  10                  15

Thr Thr Ala Ala Pro Lys Ala Arg Arg Ala His Leu Leu Ala Ala
            20                  25                  30

Arg Arg Ala Leu Ala Ala Pro Ile Arg Cys Ser Ala Ala Pro Pro Ala
        35                  40                  45

Thr Leu Thr Val Thr Ala Pro Pro Ala Thr Pro Leu Arg Pro Trp Gly
    50                  55                  60

Pro Thr Asp Pro Arg Lys Gly Ala Asp Ile Leu Val Glu Ala Leu Glu
65                  70                  75                  80

Arg Cys Gly Val Arg Asp Val Phe Ala Tyr Pro Gly Gly Ala Ser Met
                85                  90                  95

Glu Ile His Gln Ala Leu Thr Arg Ser Pro Val Ile Ala Asn His Leu
            100                 105                 110

Phe Arg His Glu Gln Gly Glu Ala Phe Ala Ala Ser Gly Phe Ala Arg
        115                 120                 125

Ser Ser Gly Arg Val Gly Val Cys Val Ala Thr Ser Gly Pro Gly Ala
    130                 135                 140

Thr Asn Leu Val Ser Ala Leu Ala Asp Ala Leu Leu Asp Ser Val Pro
145                 150                 155                 160

Met Val Ala Ile Thr Gly Gln Val Pro Arg Arg Met Ile Gly Thr Asp
                165                 170                 175

Ala Phe Gln Glu Thr Pro Ile Val Glu Val Thr Arg Ser Ile Thr Lys
            180                 185                 190

His Asn Tyr Leu Val Leu Asp Val Asp Asp Ile Pro Arg Val Val Gln
        195                 200                 205

Glu Ala Phe Phe Leu Ala Ser Ser Gly Arg Pro Gly Pro Val Leu Val
    210                 215                 220

Asp Ile Pro Lys Asp Ile Gln Gln Gln Met Ala Val Pro Val Trp Asp
225                 230                 235                 240

Thr Pro Met Ser Leu Pro Gly Tyr Ile Ala Arg Leu Pro Lys Pro Pro
                245                 250                 255

Ala Thr Glu Leu Leu Glu Gln Val Leu Arg Leu Val Gly Glu Ser Arg
            260                 265                 270

Arg Pro Val Leu Tyr Val Gly Gly Gly Cys Ala Ala Ser Gly Glu Glu
        275                 280                 285

Leu Arg Arg Phe Val Glu Met Thr Gly Ile Pro Val Thr Thr Thr Leu
    290                 295                 300
```

```
Met Gly Leu Gly Asn Phe Pro Gly Asp Asp Pro Leu Ser Leu Arg Met
305                 310                 315                 320

Leu Gly Met His Gly Thr Val Tyr Ala Asn Tyr Ala Val Asp Lys Ala
            325                 330                 335

Asp Leu Leu Leu Ala Phe Gly Val Arg Phe Asp Asp Arg Val Thr Gly
        340                 345                 350

Lys Ile Glu Ala Phe Ala Ser Arg Ala Lys Ile Val His Ile Asp Ile
    355                 360                 365

Asp Pro Ala Glu Ile Gly Lys Asn Lys Gln Pro His Val Ser Ile Cys
370                 375                 380

Ala Asp Val Lys Leu Ala Leu Gln Gly Met Asn Ala Leu Leu Glu Gly
385                 390                 395                 400

Ser Thr Ser Lys Lys Ser Phe Asp Phe Gly Ser Trp Gln Ala Glu Leu
            405                 410                 415

Asp Gln Gln Lys Arg Glu Phe Pro Leu Gly Tyr Lys Thr Phe Asp Asp
        420                 425                 430

Glu Ile Gln Pro Gln Tyr Ala Ile Gln Val Leu Asp Glu Leu Thr Lys
    435                 440                 445

Gly Glu Ala Ile Ile Ala Thr Gly Val Gly Gln His Gln Met Trp Ala
450                 455                 460

Ala Gln Tyr Tyr Thr Tyr Lys Arg Pro Arg Gln Trp Leu Ser Ser Ala
465                 470                 475                 480

Gly Leu Gly Ala Met Gly Phe Gly Leu Pro Ala Ala Gly Ala Ala
            485                 490                 495

Val Ala Asn Pro Gly Ile Thr Val Val Asp Ile Asp Gly Asp Gly Ser
            500                 505                 510

Phe Leu Met Asn Ile Gln Glu Leu Ala Met Ile Arg Ile Glu Asn Leu
        515                 520                 525

Pro Val Lys Ile Phe Val Leu Asn Asn Gln His Leu Gly Met Val Val
    530                 535                 540

Gln Trp Glu Asp Arg Phe Tyr Lys Ala Asn Arg Ala His Thr Tyr Leu
545                 550                 555                 560

Gly Asn Pro Glu Asn Glu Ser Glu Ile Tyr Pro Asp Phe Val Thr Ile
            565                 570                 575

Ala Lys Gly Phe Asn Ile Pro Ala Val Arg Val Thr Lys Lys Ser Glu
        580                 585                 590

Val His Ala Ala Ile Lys Lys Met Leu Glu Thr Pro Gly Pro Tyr Leu
    595                 600                 605

Leu Asp Ile Ile Val Pro His Gln Glu His Val Leu Pro Met Ile Pro
610                 615                 620

Ser Gly Gly Ala Phe Lys Asp Met Ile Leu Asp Gly Asp Gly Arg Thr
625                 630                 635                 640

Val Tyr

<210> SEQ ID NO 3
<211> LENGTH: 2217
<212> TYPE: DNA
<213> ORGANISM: Sorghum bicolor subsp. X drummondii

<400> SEQUENCE: 3
ccaccgccgc cgccgctgcc gccgcgctag ccggcgccac taccgctgcg cccaaggcga    60
ggcgccgggc gcacctcctg gccgcacggc gcgccctcgc cgcgcccatc aggtgctcag   120
cggcgccacc cgccacgctg acggtgacgg ctcccccggc caccccgctc cggccgtggg   180
```

-continued

```
gccccaccga tccccgcaag ggcgccgaca tcctcgtcga ggctcttgag cgctgcggcg    240
tccgcgacgt cttcgcctac cccggcggcg cgtccatgga gatccaccag gcactcaccc    300
gttcccccgt catcgccaac cacctcttcc gccacgagca agggaggcc ttcgccgcct     360
ctggcttcgc gcgctcctcg ggccgcgtcg ggtctgcgt cgccacctcc ggccccggcg     420
ccaccaacct agtctccgcg ctcgccgacg cgctgctcga ctccgtcccc atggtcgcca    480
tcacgggaca ggttctgcgg cgcatgattg caccgacgc cttccaggag acgcccatcg     540
tcgaggtcac ccgctccatc accaaacata actacctggt cctcgacgtc gacgacatcc    600
cccgcgtcgt gcaggaggct ttcttcctcg cctcctccgg tcgcccggga ccggtgcttg    660
tcgacatccc caaggacatc agcagcagag tggccgtgcc ggtctgggac acgcccatga    720
gtctgcctgg gtacattgcg cgccttccca agcctcctgc gactgaattg cttgagcagg    780
tgctgcgtct tgttggtgaa tcaaggcgcc ctgttcttta tgttggtggt ggctgcgcag    840
catctggcga ggagttgcgc cgcttgtgg agatgactgg aatcccagtc acaactactc     900
ttatgggcct tggcaatttc cctggcgacg acccactgtc tctgcgcatg cttggtatgc    960
atggcacggt gtatgcaaat tatgcagtgg ataaggcgga tctgttgctt gcatttggtg    1020
tgcggtttga tgatcgtgtg acagggaaga ttgaggcttt tgcaagcggg gctaagattg    1080
tgcacattga tattgatccc gctgagattg gcaagaacaa gcagccacat gtgtccatct    1140
gtgcagacgt taagcttgct ttgcagggca tgaatgctct tctggaagga agcacatcaa    1200
agaagagctt tgactttggc tcatggcaag ctgagttgga tcagcagaag agagagttcc    1260
cccttgggta taaaactttt gatgacgaga tccagccaca atatgctatt caggttcttg    1320
atgagctgac aaaaggggag gccatcattg ccacaggtgt tgggcagcac cagatgtggg    1380
cggcacagta ctacacttac aagcggccaa ggcagtggtt gtcttcagct ggtcttgggg    1440
ctatgggatt tggtttgccg gctgctgctg gcgctgctgt ggccaaccca ggtatcactg    1500
ttgttgacat cgacggagat ggtagcttcc tcatgaacat tcaggagcta gctatgatcc    1560
gaattgagaa cctcccagtg aaggtctttg tgctaaacaa ccagcacctg gggatggtgg    1620
tgcagtggga ggacaggttc tataaggcca acagagcgca cacatacttg ggaaacccag    1680
agaatgaaag tgagatatat ccagatttcg tgacaattgc caagggggttc aacattccag    1740
cagtccgtgt gacaaagaag agcgaagtcc atgcagcaat caagaagatg cttgagactc    1800
cagggccata cctcttggat ataatcgtcc cgcaccagga gcatgtgttg cctatgatcc    1860
ctagtggtgg ggcttttcaag gatatgatcc tggatggtga tggcaggact gtgtattgat    1920
ctaaatttca gcatgcacat ctccctgcct ttctttgaca tgcatatgag ctggtacaag    1980
ggtgatgtgt tatttatgtg atgttctcct gtgttctatc tttttgtaag ccgtcagcta    2040
tctatagtgt gcttgtttga tgtactctgt tatggtaatc ttaagtagtt tcctaccttg    2100
tagtggtgta gtctgttgtt tcgtgctggc atatctgtca tcagaggtca tgtaagtgcc    2160
ttttgctaca gataaataag gaaataagca ttgctatgca gtggttctgt acgaagc       2217
```

<210> SEQ ID NO 4
<211> LENGTH: 638
<212> TYPE: PRT
<213> ORGANISM: Sorghum bicolor subsp. X drummondii

<400> SEQUENCE: 4

Thr Ala Ala Ala Ala Ala Ala Ala Leu Ala Gly Ala Thr Thr Ala Ala
1               5                   10                  15

-continued

```
Pro Lys Ala Arg Arg Ala His Leu Leu Ala Ala Arg Ala Leu
            20                  25                  30
Ala Ala Pro Ile Arg Cys Ser Ala Ala Pro Ala Thr Leu Thr Val
            35                  40                  45
Thr Ala Pro Pro Ala Thr Pro Leu Arg Pro Trp Gly Pro Thr Asp Pro
 50                  55                  60
Arg Lys Gly Ala Asp Ile Leu Val Glu Ala Leu Glu Arg Cys Gly Val
 65                  70                  75                  80
Arg Asp Val Phe Ala Tyr Pro Gly Gly Ala Ser Met Glu Ile His Gln
                85                  90                  95
Ala Leu Thr Arg Ser Pro Val Ile Ala Asn His Leu Phe Arg His Glu
            100                 105                 110
Gln Gly Glu Ala Phe Ala Ala Ser Gly Phe Ala Arg Ser Ser Gly Arg
            115                 120                 125
Val Gly Val Cys Val Ala Thr Ser Gly Pro Gly Ala Thr Asn Leu Val
            130                 135                 140
Ser Ala Leu Ala Asp Ala Leu Leu Asp Ser Val Pro Met Val Ala Ile
145                 150                 155                 160
Thr Gly Gln Val Leu Arg Arg Met Ile Gly Thr Asp Ala Phe Gln Glu
                165                 170                 175
Thr Pro Ile Val Glu Val Thr Arg Ser Ile Thr Lys His Asn Tyr Leu
            180                 185                 190
Val Leu Asp Val Asp Asp Ile Pro Arg Val Val Gln Glu Ala Phe Phe
            195                 200                 205
Leu Ala Ser Ser Gly Arg Pro Gly Pro Val Leu Val Asp Ile Pro Lys
210                 215                 220
Asp Ile Gln Gln Gln Met Ala Val Pro Val Trp Asp Thr Pro Met Ser
225                 230                 235                 240
Leu Pro Gly Tyr Ile Ala Arg Leu Pro Lys Pro Pro Ala Thr Glu Leu
                245                 250                 255
Leu Glu Gln Val Leu Arg Leu Val Gly Glu Ser Arg Arg Pro Val Leu
            260                 265                 270
Tyr Val Gly Gly Gly Cys Ala Ala Ser Gly Glu Glu Leu Arg Arg Phe
            275                 280                 285
Val Glu Met Thr Gly Ile Pro Val Thr Thr Thr Leu Met Gly Leu Gly
            290                 295                 300
Asn Phe Pro Gly Asp Asp Pro Leu Ser Leu Arg Met Leu Gly Met His
305                 310                 315                 320
Gly Thr Val Tyr Ala Asn Tyr Ala Val Asp Lys Ala Asp Leu Leu Leu
                325                 330                 335
Ala Phe Gly Val Arg Phe Asp Asp Arg Val Thr Gly Lys Ile Glu Ala
            340                 345                 350
Phe Ala Ser Gly Ala Lys Ile Val His Ile Asp Ile Asp Pro Ala Glu
            355                 360                 365
Ile Gly Lys Asn Lys Gln Pro His Val Ser Ile Cys Ala Asp Val Lys
            370                 375                 380
Leu Ala Leu Gln Gly Met Asn Ala Leu Leu Glu Gly Ser Thr Ser Lys
385                 390                 395                 400
Lys Ser Phe Asp Phe Gly Ser Trp Gln Ala Glu Leu Asp Gln Gln Lys
                405                 410                 415
Arg Glu Phe Pro Leu Gly Tyr Lys Thr Phe Asp Asp Glu Ile Gln Pro
            420                 425                 430
Gln Tyr Ala Ile Gln Val Leu Asp Glu Leu Thr Lys Gly Glu Ala Ile
```

```
                435                 440                 445
Ile Ala Thr Gly Val Gly Gln His Gln Met Trp Ala Ala Gln Tyr Tyr
                450                 455                 460

Thr Tyr Lys Arg Pro Arg Gln Trp Leu Ser Ser Ala Gly Leu Gly Ala
465                 470                 475                 480

Met Gly Phe Gly Leu Pro Ala Ala Ala Gly Ala Val Ala Asn Pro
                    485                 490                 495

Gly Ile Thr Val Val Asp Ile Asp Gly Asp Gly Ser Phe Leu Met Asn
                500                 505                 510

Ile Gln Glu Leu Ala Met Ile Arg Ile Glu Asn Leu Pro Val Lys Val
                515                 520                 525

Phe Val Leu Asn Asn Gln His Leu Gly Met Val Val Gln Trp Glu Asp
530                 535                 540

Arg Phe Tyr Lys Ala Asn Arg Ala His Thr Tyr Leu Gly Asn Pro Glu
545                 550                 555                 560

Asn Glu Ser Glu Ile Tyr Pro Asp Phe Val Thr Ile Ala Lys Gly Phe
                565                 570                 575

Asn Ile Pro Ala Val Arg Val Thr Lys Lys Ser Glu Val His Ala Ala
                580                 585                 590

Ile Lys Lys Met Leu Glu Thr Pro Gly Pro Tyr Leu Leu Asp Ile Ile
                595                 600                 605

Val Pro His Gln Glu His Val Leu Pro Met Ile Pro Ser Gly Gly Ala
            610                 615                 620

Phe Lys Asp Met Ile Leu Asp Gly Asp Gly Arg Thr Val Tyr
625                 630                 635

<210> SEQ ID NO 5
<211> LENGTH: 2219
<212> TYPE: DNA
<213> ORGANISM: Sorghum bicolor subsp. X drummondii

<400> SEQUENCE: 5
tggccaccac cgccgccgcc gctgccgccg cgctagccgg cgccactacc gctgcgccca      60
aggcgaggcg ccgggcgcac ctcctggccg cacggcgcgc cctcgccgcg cccatcaggt     120
gctcagcggc gccacccgcc acgctgacgg tgacggctcc cccggccacc ccgctccggc     180
cgtggggccc caccgatccc cgcaagggcg ccgacatcct cgtcgaggct cttgagcgct     240
gcggcgtccg cgacgtcttc gcctaccccg gcggcgcgtc catggagatc caccaggcac     300
tcacccgttc cccgtcatc gccaaccacc tcttccgcca cgagcaaggg gaggccttcg     360
ccgcctctgg cttcgcgcgc tcctcgggcc gcgtcggcgt ctgcgtcgcc acctccggcc     420
ccggcgccac caacctagtc tccgcgctcg ccgacgcgct gctcgactcc gtccccatgg     480
tcgccatcac gggacaggtt ctgcggcgca tgattggcac cgacgccttc caggagacgc     540
ccatcgtcga ggtcacccgc tccatcacca aacataacta cctggtcctc gacgtcgacg     600
acatcccccg cgtcgtgcag gaggctttct tcctcgcctc ctccggtcgc ccgggaccgg     660
tgcttgtcga catccccaag gacatccagc agcagatggc cgtgccggtc tgggacacgc     720
ccatgagtct gcctgggtac attgcgcgcc ttcccaagcc tcctgcgact gaattgcttg     780
agcaggtgct gcgtcttgtt ggtgaatcaa ggcgccctgt tctttatgtt ggtggtggct     840
gcgcagcatc tggcgaggag ttgcgccgct tgtggagat gactggaatc ccagtcacaa     900
ctactcttat gggccttggc aatttccctg cgacgaccc actgtctctg cgcatgcttg     960
gtatgcatgg cacggtgtat gcaaattatg cagtggataa ggcggatctg ttgcttgcat    1020
```

```
ttggtgtgcg gtttgatgat cgtgtgacag ggaagattga ggcttttgca agcagggcta   1080
agattgtgca cattgatatt gatcccgctg agattggcaa gaacaagcag ccacatgtgt   1140
ccatctgtgc agacgttaag cttgctttgc agggcatgaa tgctcttctg gaaggaagca   1200
catcaaagaa gagctttgac tttggctcat ggcaagctga gttggatcag cagaagagag   1260
agttccccct tgggtataaa acttttgatg acgagatcca gccacaatat gctattcagg   1320
ttcttgatga gctgacaaaa ggggaggcca tcattgccac aggtgttggg cagcaccaga   1380
tgtgggcggc acagtactac acttacaagc ggccaaggca gtggttgtct tcagctggtc   1440
ttggggctat gggatttggt ttgccggctg ctgctggcgc tgctgtggcc aacccaggta   1500
tcactgttgt tgacatcgac ggagatggta gcttcctcat gaacattcag gagctagcta   1560
tgatccgaat tgagaacctc ccagtgaagg tctttgtgct aaacaaccag cacctgggga   1620
tggtggtgca gtgggaggac aggttctata aggccaacag agcgcacaca tacttgggaa   1680
acccagagaa tgaaagtgag atatatccag atttcgtgac aattgccaaa gggttcaaca   1740
ttccagcagt ccgtgtgaca agaagagcg aagtccatgc agcaatcaag aagatgcttg   1800
agactccagg gccataccctc ttggatataa tcgtcccgca ccaggagcat gtgttgccta   1860
tgatccctag tggtggggct ttcaaggata tgatcctgga tggtgatggc aggactgtgt   1920
attgatctaa atttcagcat gcacatctcc ctgcctttct ttgacatgca tatgagctgg   1980
tacaagggtg atgtgttatt tatgtgatgt tctcctgtgt tctatctttt tgtaagccgt   2040
cagctatcta tagtgtgctt gtttgatgta ctctgttatg gtaatcttaa gtagtttcct   2100
accttgtagt ggtgtagtct gttgtttcgt gctggcatat ctgtcatcag aggtcatgta   2160
agtgccttt gctacagata aataaggaaa taagcattgc tatgcagtgg ttctgtacg    2219
```

<210> SEQ ID NO 6
<211> LENGTH: 640
<212> TYPE: PRT
<213> ORGANISM: Sorghum bicolor subsp. X drummondii

<400> SEQUENCE: 6

Ala Thr Thr Ala Ala Ala Ala Ala Ala Leu Ala Gly Ala Thr Thr
1               5                   10                  15

Ala Ala Pro Lys Ala Arg Arg Ala His Leu Leu Ala Leu Arg Arg
            20                  25                  30

Ala Leu Ala Ala Pro Ile Arg Cys Ser Ala Pro Pro Ala Thr Leu
        35                  40                  45

Thr Val Thr Ala Pro Pro Ala Thr Pro Leu Arg Pro Trp Gly Pro Thr
    50                  55                  60

Asp Pro Arg Lys Gly Ala Asp Ile Leu Val Glu Ala Leu Glu Arg Cys
65                  70                  75                  80

Gly Val Arg Asp Val Phe Ala Tyr Pro Gly Gly Ala Ser Met Glu Ile
                85                  90                  95

His Gln Ala Leu Thr Arg Ser Pro Val Ile Ala Asn His Leu Phe Arg
            100                 105                 110

His Glu Gln Gly Glu Ala Phe Ala Ala Ser Gly Phe Ala Arg Ser Ser
        115                 120                 125

Gly Arg Val Gly Val Cys Val Ala Thr Ser Gly Pro Gly Ala Thr Asn
    130                 135                 140

Leu Val Ser Ala Leu Ala Asp Ala Leu Leu Asp Ser Val Pro Met Val
145                 150                 155                 160

```
Ala Ile Thr Gly Gln Val Leu Arg Arg Met Ile Gly Thr Asp Ala Phe
                165                 170                 175
Gln Glu Thr Pro Ile Val Glu Val Thr Arg Ser Ile Thr Lys His Asn
            180                 185                 190
Tyr Leu Val Leu Asp Val Asp Asp Ile Pro Arg Val Val Gln Glu Ala
        195                 200                 205
Phe Phe Leu Ala Ser Ser Gly Arg Pro Gly Pro Val Leu Val Asp Ile
    210                 215                 220
Pro Lys Asp Ile Gln Gln Met Ala Val Pro Val Trp Asp Thr Pro
225                 230                 235                 240
Met Ser Leu Pro Gly Tyr Ile Ala Arg Leu Pro Lys Pro Pro Ala Thr
                245                 250                 255
Glu Leu Leu Glu Gln Val Leu Arg Leu Val Gly Glu Ser Arg Arg Pro
            260                 265                 270
Val Leu Tyr Val Gly Gly Gly Cys Ala Ala Ser Gly Glu Glu Leu Arg
        275                 280                 285
Arg Phe Val Glu Met Thr Gly Ile Pro Val Thr Thr Thr Leu Met Gly
    290                 295                 300
Leu Gly Asn Phe Pro Gly Asp Asp Pro Leu Ser Leu Arg Met Leu Gly
305                 310                 315                 320
Met His Gly Thr Val Tyr Ala Asn Tyr Ala Val Asp Lys Ala Asp Leu
                325                 330                 335
Leu Leu Ala Phe Gly Val Arg Phe Asp Asp Arg Val Thr Gly Lys Ile
            340                 345                 350
Glu Ala Phe Ala Ser Arg Ala Lys Ile Val His Ile Asp Ile Asp Pro
        355                 360                 365
Ala Glu Ile Gly Lys Asn Lys Gln Pro His Val Ser Ile Cys Ala Asp
    370                 375                 380
Val Lys Leu Ala Leu Gln Gly Met Asn Ala Leu Leu Glu Gly Ser Thr
385                 390                 395                 400
Ser Lys Lys Ser Phe Asp Phe Gly Ser Trp Gln Ala Glu Leu Asp Gln
                405                 410                 415
Gln Lys Arg Glu Phe Pro Leu Gly Tyr Lys Thr Phe Asp Asp Glu Ile
            420                 425                 430
Gln Pro Gln Tyr Ala Ile Gln Val Leu Asp Glu Leu Thr Lys Gly Glu
        435                 440                 445
Ala Ile Ile Ala Thr Gly Val Gly Gln His Gln Met Trp Ala Ala Gln
    450                 455                 460
Tyr Tyr Thr Tyr Lys Arg Pro Arg Gln Trp Leu Ser Ser Ala Gly Leu
465                 470                 475                 480
Gly Ala Met Gly Phe Gly Leu Pro Ala Ala Gly Ala Ala Val Ala
                485                 490                 495
Asn Pro Gly Ile Thr Val Val Asp Ile Asp Gly Asp Gly Ser Phe Leu
            500                 505                 510
Met Asn Ile Gln Glu Leu Ala Met Ile Arg Ile Glu Asn Leu Pro Val
        515                 520                 525
Lys Val Phe Val Leu Asn Asn Gln His Leu Gly Met Val Val Gln Trp
    530                 535                 540
Glu Asp Arg Phe Tyr Lys Ala Asn Arg Ala His Thr Tyr Leu Gly Asn
545                 550                 555                 560
Pro Glu Asn Glu Ser Glu Ile Tyr Pro Asp Phe Val Thr Ile Ala Lys
                565                 570                 575
Gly Phe Asn Ile Pro Ala Val Arg Val Thr Lys Lys Ser Glu Val His
```

```
                580             585             590
Ala Ala Ile Lys Lys Met Leu Glu Thr Pro Gly Pro Tyr Leu Leu Asp
            595                 600                 605

Ile Ile Val Pro His Gln Glu His Val Leu Pro Met Ile Pro Ser Gly
            610                 615                 620

Gly Ala Phe Lys Asp Met Ile Leu Asp Gly Asp Gly Arg Thr Val Tyr
625                 630                 635                 640

<210> SEQ ID NO 7
<211> LENGTH: 2218
<212> TYPE: DNA
<213> ORGANISM: Sorghum bicolor subsp. X drummondii

<400> SEQUENCE: 7
accaccgccg ccgccgctgc cgccgcgcta gccggcgcca ctaccgctgc gcccaaggcg        60
aggcgccggg cgcacctcct ggccgcacgg cgcgccctcg ccgcgcccat caggtgctca      120
gcggcgccac ccgccacgct gacggtgacg gctcccccgg ccaccccgct ccggccgtgg      180
ggccccaccg atccccgcaa gggcgccgac atcctcgtcg aggctcttga gcgctgcggc      240
gtccgcgacg tcttcgccta ccccggcggc gcgtccatgg agatccacca ggcactcacc      300
cgttccccg tcatcgccaa ccacctcttc cgccacgagc aaggggaggc cttcgccgcc       360
tctggcttcg cgcgctcctc gggcgcgtc ggcgtctgcg tcgccacctc cggcccggc        420
gccaccaacc tagtctccgc gctcgccgac gcgctgctcg actccgtccc catggtcgcc      480
atcacgggac aggttccgcg cgcatgatt ggcaccgacg ccttccagga gacgcccatc       540
gtcgaggtca cccgctccat caccaaacat aactacctgg tcctcgacgt cgacgacatc      600
ccccgcgtcg tgcaggaggc tttcttcctc gcctcctccg gtcgcccggg accggtgctt     660
gtcgacatcc ccaaggacat ccagcagcag atggccgtgc cggtctggga cacgcccatg     720
agtctgcctg gtacattgc gcgccttccc aagcctcctg cgactgaatt gcttgagcag      780
gtgctgcgtc ttgttggtga atcaaggcgc cctgttcttt atgttggtgg tggctgcgca     840
gcatctggcg aggagttgcg ccgctttgtg gagatgactg gaatcccagt cacaactact     900
cttatgggcc ttggcaattt ccctggcgac gacccactgt ctctgcgcat gcttggtatg     960
catggcacgg tgtatgcaaa ttatgcagtg gataaggcgg atctgttgct gcatttggt    1020
gtgcggtttg atgatcgtgt gacagggaag attgaggctt ttgcaagcag ggctaagatt    1080
gtgcacattg atattgatcc cgctgagatt ggcaagaaca agcagccaca tgtgtccatc   1140
tgtgcagacg ttaagcttgc tttgcagggc atgaatgctc ttctggaagg aagcacatca   1200
aagaagagct ttgactttgg ctcatggcaa gctgagttgg atcagcagaa gagagagttc   1260
cccttgggt ataaaacttt tgatgacgag atccagccac aatatgctat tcaggttctt   1320
gatgagctga caaaagggga ggccatcatt gccacaggtg ttgggcagca ccagatgtgg   1380
gcggcacagt actacactta caagcggcca aggcagtggt tgtcttcagc tggtcttggg   1440
gctatgggat ttggttttgcc ggctgctgct ggcgctgctg tggccaaccc aggtatcact   1500
gttgttgaca tcgacggaga tggtagcttc ctcatgaaca ttcaggagct agctatgatc   1560
cgaattgaga acctcccagt gaaggtcttt gtgctaaaca accagcacct ggggatggtg   1620
gtgcagttgg aggacaggtt ctataaggcc aacagagcgc acacatactt gggaaaccca   1680
gagaatgaaa gtgagatata tccagatttc gtgacaattg ccaaagggtt caacattcca   1740
gcagtccgtg tgacaaagaa gagcgaagtc catgcagcaa tcaagaagat gcttgagact   1800
```

```
ccagggccat acctcttgga tataatcgtc ccgcaccagg agcatgtgtt gcctatgatc      1860
cctagtggtg gggctttcaa ggatatgatc ctggatggtg atggcaggac tgtgtattga      1920
tctaaatttc agcatgcaca tctccctgcc tttctttgac atgcatatga gctggtacaa      1980
gggtgatgtg ttatttatgt gatgttctcc tgtgttctat cttttttgtaa gccgtcagct     2040 atctatagtg tgcttgtttg atgtactctg ttatggtaat cttaagtagt ttcctacctt      2100
gtagtggtgt agtctgttgt ttcgtgctgg catatctgtc atcagaggtc atgtaagtgc      2160
cttttgctac agataaataa ggaaataagc attgctatgc agtggttctg tacgaagc        2218
```

<210> SEQ ID NO 8
<211> LENGTH: 640
<212> TYPE: PRT
<213> ORGANISM: Sorghum bicolor subsp. X drummondii
<220> FEATURE:
<221> NAME/KEY: VARIANT
<222> LOCATION: 510
<223> OTHER INFORMATION: Xaa= any amino acid

<400> SEQUENCE: 8

```
Ala Thr Thr Ala Ala Ala Ala Ala Ala Leu Ala Gly Ala Thr Thr
 1               5                  10                  15

Ala Ala Pro Lys Ala Arg Arg Ala His Leu Leu Ala Ala Arg Arg
                20                  25                  30

Ala Leu Ala Ala Pro Ile Arg Cys Ser Ala Ala Pro Ala Thr Leu
                35                  40                  45

Thr Val Thr Ala Pro Pro Ala Thr Pro Leu Arg Pro Trp Gly Pro Thr
            50                  55                  60

Asp Pro Arg Lys Gly Ala Asp Ile Leu Val Glu Ala Leu Glu Arg Cys
 65                  70                  75                  80

Gly Val Arg Asp Val Phe Ala Tyr Pro Gly Gly Ala Ser Met Glu Ile
                    85                  90                  95

His Gln Ala Leu Thr Arg Ser Pro Val Ile Ala Asn His Leu Phe Arg
                100                 105                 110

His Glu Gln Gly Glu Ala Phe Ala Ala Ser Gly Phe Ala Arg Ser Ser
            115                 120                 125

Gly Arg Val Gly Val Cys Val Ala Thr Ser Gly Pro Gly Ala Thr Asn
        130                 135                 140

Leu Val Ser Ala Leu Ala Asp Ala Leu Leu Asp Ser Val Pro Met Val
145                 150                 155                 160

Ala Ile Thr Gly Gln Val Pro Arg Arg Met Ile Gly Thr Asp Ala Phe
                165                 170                 175

Gln Glu Thr Pro Ile Val Glu Val Thr Arg Ser Ile Thr Lys His Asn
            180                 185                 190

Tyr Leu Val Leu Asp Val Asp Asp Ile Pro Arg Val Val Gln Glu Ala
        195                 200                 205

Phe Phe Leu Ala Ser Ser Gly Arg Pro Gly Pro Val Leu Val Asp Ile
    210                 215                 220

Pro Lys Asp Ile Gln Gln Gln Met Ala Val Pro Val Trp Asp Thr Pro
225                 230                 235                 240

Met Ser Leu Pro Gly Tyr Ile Ala Arg Leu Pro Lys Pro Pro Ala Thr
                245                 250                 255

Glu Leu Leu Glu Gln Val Leu Arg Leu Val Gly Glu Ser Arg Arg Pro
            260                 265                 270

Val Leu Tyr Val Gly Gly Gly Cys Ala Ala Ser Gly Glu Glu Leu Arg
        275                 280                 285
```

```
Arg Phe Val Glu Met Thr Gly Ile Pro Val Thr Thr Thr Leu Met Gly
        290                 295                 300

Leu Gly Asn Phe Pro Gly Asp Asp Pro Leu Ser Leu Arg Met Leu Gly
305                 310                 315                 320

Met His Gly Thr Val Tyr Ala Asn Tyr Ala Val Asp Lys Ala Asp Leu
                325                 330                 335

Leu Leu Ala Phe Gly Val Arg Phe Asp Asp Arg Val Thr Gly Lys Ile
                340                 345                 350

Glu Ala Phe Ala Ser Arg Ala Lys Ile Val His Ile Asp Ile Asp Pro
                355                 360                 365

Ala Glu Ile Gly Lys Asn Lys Gln Pro His Val Ser Ile Cys Ala Asp
            370                 375                 380

Val Lys Leu Ala Leu Gln Gly Met Asn Ala Leu Leu Glu Gly Ser Thr
385                 390                 395                 400

Ser Lys Lys Ser Phe Asp Phe Gly Ser Trp Gln Ala Glu Leu Asp Gln
                405                 410                 415

Gln Lys Arg Glu Phe Pro Leu Gly Tyr Lys Thr Phe Asp Asp Glu Ile
                420                 425                 430

Gln Pro Gln Tyr Ala Ile Gln Val Leu Asp Glu Leu Thr Lys Gly Glu
                435                 440                 445

Ala Ile Ile Ala Thr Gly Val Gly Gln His Gln Met Trp Ala Ala Gln
450                 455                 460

Tyr Tyr Thr Tyr Lys Arg Pro Arg Gln Trp Leu Ser Ser Ala Gly Leu
465                 470                 475                 480

Gly Ala Met Gly Phe Gly Leu Pro Ala Ala Gly Ala Ala Val Ala
                485                 490                 495

Asn Pro Gly Ile Thr Val Val Asp Ile Asp Gly Asp Gly Xaa Phe Leu
                500                 505                 510

Met Asn Ile Gln Glu Leu Ala Met Ile Arg Ile Glu Asn Leu Pro Val
                515                 520                 525

Lys Val Phe Val Leu Asn Asn Gln His Leu Gly Met Val Val Gln Leu
                530                 535                 540

Glu Asp Arg Phe Tyr Lys Ala Asn Arg Ala His Thr Tyr Leu Gly Asn
545                 550                 555                 560

Pro Glu Asn Glu Ser Glu Ile Tyr Pro Asp Phe Val Thr Ile Ala Lys
                565                 570                 575

Gly Phe Asn Ile Pro Ala Val Arg Val Thr Lys Lys Ser Glu Val His
                580                 585                 590

Ala Ala Ile Lys Lys Met Leu Glu Thr Pro Gly Pro Tyr Leu Leu Asp
                595                 600                 605

Ile Ile Val Pro His Gln Glu His Val Leu Pro Met Ile Pro Ser Gly
                610                 615                 620

Gly Ala Phe Lys Asp Met Ile Leu Asp Gly Asp Gly Arg Thr Val Tyr
625                 630                 635                 640

<210> SEQ ID NO 9
<211> LENGTH: 2218
<212> TYPE: DNA
<213> ORGANISM: Sorghum bicolor subsp. X drummondii

<400> SEQUENCE: 9
accaccgccg ccgccgccgc cgccgcgcta gccggcgcca ctaccgctgc gcccaaggcg      60
aggcgccggg cgcacctcct ggccgcacgg cgcgccctcg ccgcgcccat caggtgctca    120
```

```
gcggcgccac cgccacgct  gacggtgacg gctccccgg  ccaccccgct ccggccgtgg    180
ggccccaccg atccccgcaa gggcgccgac atcctcgtcg aggctcttga gcgctgcggc    240
gtccgcgacg tcttcgccta ccccggcggc gcgtccatgg agatccacca ggcactcacc    300
cgttccccg  tcatcgccaa ccacctcttc cgccacgagc aaggggaggc cttcgccgcc    360
tctggcttcg cgcgctcctc gggccgcgtc ggcgtctgcg tcgccacctc cggccccggc    420
gccaccaacc tagtctccgc gctcgccgac gcgctgctcg actccgtccc catggtcgcc    480
atcacgggac aggttccgcg gcgcatgatt ggcaccgacg ccttccagga gacgcccatc    540
gtcgaggtca cccgctccat caccaaacat aactacctgg tcctcgacgt cgacgacatc    600
ccccgcgtcg tgcaggaggc tttcttcctc gcctcctccg gtcgcccggg accggtgctt    660
gtcgacatcc ccaaggacat ccagcagcag atggccgtgc cggtctggga cacgcccatg    720
agtctgcctg ggtacattgc gcgccttccc aagcctcctg cgactgaatt gcttgagcag    780
gtgctgcgtc ttgttggtga atcaaggcgc cctgttcttt atgttggtgg tggctgcgca    840
gcatctggcg aggagttgcg ccgctttgtg agatgactg  gaatcccagt cacaactact    900
cttatgggcc ttggcaattt ccctggcgac gacccactgt ctctgcgcat gcttggtatg    960
catggcacgg tgtatgcaaa ttatgcagtg gataaggcgg atctgttgct tgcatttggt   1020
gtgcggtttg atgatcgtgt gacagggaag attgaggctt tgcaagcag  ggctaagatt   1080
gtgcacattg atattgatcc cgctgagatt ggcaagaaca agcagccaca tgtgtccatc   1140
tgtgcagacg ttaagcttgc tttgcagggc atgaatgctc ttctggaagg aagcacatca   1200
aagaagagct ttgactttgg ctcatggcaa gctgagttgg atcagcagaa gagagagttc   1260
cccctttgggt ataaaacttt tgatgacgag atccagccac aatatgctat tcaggttctt   1320
gatgagctga caaaagggga ggccatcatt gccacaggtg ttgggcagca ccagatgtgg   1380
gcggcacagt actacactta caagcggcca aggcagtggt tgtcttcagc tggtcttggg   1440
gctatgggat ttggtttgcc ggctgctgct ggcgctgctg tggccaaccc aggtatcact   1500
gttgttgaca tcgacggaga tggtagcttc ctcatgaaca ttcaggagct agctatgatc   1560
cgaattgaga acctcccagt gaagatcttt gtgctaaaca accagcacct ggggatggtg   1620
gtgcagttgg aggacaggtt ctataaggcc aacagagcgc acacatactt gggaaaccca   1680
gagaatgaaa gtgagatata tccagatttc gtgacaattg ccaaagggtt caacattcca   1740
gcagtccgtg tgacaaagaa gagcgaagtc catgcagcaa tcaagaagat gcttgagact   1800
ccagggccat acctcttgga tataatcgtc ccgcaccagg agcatgtgtt gcctatgatc   1860
cctagtggtg gggctttcaa ggatatgatc ctggatggtg atggcaggac tgtgtattga   1920
tctaaatttc agcatgcaca ctccctgcc  tttctttgac atgcatatga gctggtacaa   1980
gggtgatgtg ttatttatgt gatgttctcc tgtgttctat cttttttgtaa gccgtcagct   2040
atctatagtg tgcttgtttg atgtactctg ttatggtaat cttaagtagt ttcctacctt   2100
gtagtggtgt agtctgttgt ttcgtgctgg catatctgtc atcagaggtc atgtaagtgc   2160
cttttgctac agataaataa ggaaataagc attgctatgc agtggttctg tacgaagc    2218
```

<210> SEQ ID NO 10
<211> LENGTH: 639
<212> TYPE: PRT
<213> ORGANISM: Sorghum bicolor subsp. X drummondii

<400> SEQUENCE: 10

Thr Thr Ala Ala Ala Ala Ala Ala Ala Leu Ala Gly Ala Thr Thr Ala

```
  1               5                   10                  15
Ala Pro Lys Ala Arg Arg Ala His Leu Ala Ala Arg Arg Ala
                20                  25                  30
Leu Ala Ala Pro Ile Arg Cys Ser Ala Ala Pro Pro Ala Thr Leu Thr
                35                  40                  45
Val Thr Ala Pro Pro Ala Thr Pro Leu Arg Pro Trp Gly Pro Thr Asp
 50                  55                  60
Pro Arg Lys Gly Ala Asp Ile Leu Val Glu Ala Leu Glu Arg Cys Gly
 65                  70                  75                  80
Val Arg Asp Val Phe Ala Tyr Pro Gly Gly Ala Ser Met Glu Ile His
                85                  90                  95
Gln Ala Leu Thr Arg Ser Pro Val Ile Ala Asn His Leu Phe Arg His
                100                 105                 110
Glu Gln Gly Glu Ala Phe Ala Ala Ser Gly Phe Ala Arg Ser Ser Gly
                115                 120                 125
Arg Val Gly Val Cys Val Ala Thr Ser Gly Pro Gly Ala Thr Asn Leu
                130                 135                 140
Val Ser Ala Leu Ala Asp Ala Leu Leu Asp Ser Val Pro Met Val Ala
145                 150                 155                 160
Ile Thr Gly Gln Val Pro Arg Arg Met Ile Gly Thr Asp Ala Phe Gln
                165                 170                 175
Glu Thr Pro Ile Val Glu Val Thr Arg Ser Ile Thr Lys His Asn Tyr
                180                 185                 190
Leu Val Leu Asp Val Asp Asp Ile Pro Arg Val Val Gln Glu Ala Phe
                195                 200                 205
Phe Leu Ala Ser Ser Gly Arg Pro Gly Pro Val Leu Val Asp Ile Pro
                210                 215                 220
Lys Asp Ile Gln Gln Gln Met Ala Val Pro Val Trp Asp Thr Pro Met
225                 230                 235                 240
Ser Leu Pro Gly Tyr Ile Ala Arg Leu Pro Lys Pro Pro Ala Thr Glu
                245                 250                 255
Leu Leu Glu Gln Val Leu Arg Leu Val Gly Glu Ser Arg Arg Pro Val
                260                 265                 270
Leu Tyr Val Gly Gly Gly Cys Ala Ala Ser Gly Glu Glu Leu Arg Arg
                275                 280                 285
Phe Val Glu Met Thr Gly Ile Pro Val Thr Thr Thr Leu Met Gly Leu
                290                 295                 300
Gly Asn Phe Pro Gly Asp Asp Pro Leu Ser Leu Arg Met Leu Gly Met
305                 310                 315                 320
His Gly Thr Val Tyr Ala Asn Tyr Ala Val Asp Lys Ala Asp Leu Leu
                325                 330                 335
Leu Ala Phe Gly Val Arg Phe Asp Asp Arg Val Thr Gly Lys Ile Glu
                340                 345                 350
Ala Phe Ala Ser Arg Ala Lys Ile Val His Ile Asp Ile Asp Pro Ala
                355                 360                 365
Glu Ile Gly Lys Asn Lys Gln Pro His Val Ser Ile Cys Ala Asp Val
                370                 375                 380
Lys Leu Ala Leu Gln Gly Met Asn Ala Leu Leu Glu Gly Ser Thr Ser
385                 390                 395                 400
Lys Lys Ser Phe Asp Phe Gly Ser Trp Gln Ala Glu Leu Asp Gln Gln
                405                 410                 415
Lys Arg Glu Phe Pro Leu Gly Tyr Lys Thr Phe Asp Asp Glu Ile Gln
                420                 425                 430
```

```
Pro Gln Tyr Ala Ile Gln Val Leu Asp Glu Leu Thr Lys Gly Glu Ala
        435                 440                 445

Ile Ile Ala Thr Gly Val Gly Gln His Gln Met Trp Ala Ala Gln Tyr
    450                 455                 460

Tyr Thr Tyr Lys Arg Pro Arg Gln Trp Leu Ser Ser Ala Gly Leu Gly
465                 470                 475                 480

Ala Met Gly Phe Gly Leu Pro Ala Ala Ala Gly Ala Ala Val Ala Asn
                485                 490                 495

Pro Gly Ile Thr Val Val Asp Ile Asp Gly Asp Gly Ser Phe Leu Met
                500                 505                 510

Asn Ile Gln Glu Leu Ala Met Ile Arg Ile Glu Asn Leu Pro Val Lys
            515                 520                 525

Ile Phe Val Leu Asn Asn Gln His Leu Gly Met Val Val Gln Leu Glu
        530                 535                 540

Asp Arg Phe Tyr Lys Ala Asn Arg Ala His Thr Tyr Leu Gly Asn Pro
545                 550                 555                 560

Glu Asn Glu Ser Glu Ile Tyr Pro Asp Phe Val Thr Ile Ala Lys Gly
                565                 570                 575

Phe Asn Ile Pro Ala Val Arg Val Thr Lys Lys Ser Glu Val His Ala
                580                 585                 590

Ala Ile Lys Lys Met Leu Glu Thr Pro Gly Pro Tyr Leu Leu Asp Ile
            595                 600                 605

Ile Val Pro His Gln Glu His Val Leu Pro Met Ile Pro Ser Gly Gly
        610                 615                 620

Ala Phe Lys Asp Met Ile Leu Asp Gly Asp Gly Arg Thr Val Tyr
625                 630                 635

<210> SEQ ID NO 11
<211> LENGTH: 20
<212> TYPE: DNA
<213> ORGANISM: Artificial Sequence
<220> FEATURE:
<223> OTHER INFORMATION: oligonucleotide

<400> SEQUENCE: 11
gtgcccccgc cccaaacccct                                              20

<210> SEQ ID NO 12
<211> LENGTH: 20
<212> TYPE: DNA
<213> ORGANISM: Artificial Sequence
<220> FEATURE:
<223> OTHER INFORMATION: oligonucleotide

<400> SEQUENCE: 12
actaggttgg tggcgccggg                                               20

<210> SEQ ID NO 13
<211> LENGTH: 20
<212> TYPE: DNA
<213> ORGANISM: Artificial Sequence
<220> FEATURE:
<223> OTHER INFORMATION: oligonucleotide

<400> SEQUENCE: 13
cacctccggc cccggcgcca                                               20

<210> SEQ ID NO 14
<211> LENGTH: 20
```

-continued

```
<212> TYPE: DNA
<213> ORGANISM: Artificial Sequence
<220> FEATURE:
<223> OTHER INFORMATION: oligonucleotide

<400> SEQUENCE: 14
caatcttccc tgtcacacga                                        20

<210> SEQ ID NO 15
<211> LENGTH: 22
<212> TYPE: DNA
<213> ORGANISM: Artificial Sequence
<220> FEATURE:
<223> OTHER INFORMATION: oligonucleotide

<400> SEQUENCE: 15
ggtttgatga tcgtgtgaca gg                                     22

<210> SEQ ID NO 16
<211> LENGTH: 23
<212> TYPE: DNA
<213> ORGANISM: Artificial Sequence
<220> FEATURE:
<223> OTHER INFORMATION: oligonucleotide

<400> SEQUENCE: 16
tacgccccaa gaccagctga aga                                    23

<210> SEQ ID NO 17
<211> LENGTH: 22
<212> TYPE: DNA
<213> ORGANISM: Artificial Sequence
<220> FEATURE:
<223> OTHER INFORMATION: oligonucleotide

<400> SEQUENCE: 17
gcagtggttg tcttcagctg gt                                     22

<210> SEQ ID NO 18
<211> LENGTH: 23
<212> TYPE: DNA
<213> ORGANISM: Artificial Sequence
<220> FEATURE:
<223> OTHER INFORMATION: oligonucleotide

<400> SEQUENCE: 18
gatcataggc aacacatgat cct                                    23

<210> SEQ ID NO 19
<211> LENGTH: 20
<212> TYPE: DNA
<213> ORGANISM: Artificial Sequence
<220> FEATURE:
<223> OTHER INFORMATION: oligonucleotide

<400> SEQUENCE: 19
gtgatggcag gactgtgtat                                        20

<210> SEQ ID NO 20
<211> LENGTH: 20
<212> TYPE: DNA
<213> ORGANISM: Artificial Sequence
<220> FEATURE:
<223> OTHER INFORMATION: oligonucleotide

<400> SEQUENCE: 20
```

```
cgtacagaac cactgcatag                                                    20

<210> SEQ ID NO 21
<211> LENGTH: 23
<212> TYPE: DNA
<213> ORGANISM: Artificial Sequence
<220> FEATURE:
<223> OTHER INFORMATION: oligonucleotide

<400> SEQUENCE: 21
tccgtgtgac aaagaagagc gaa                                                23

<210> SEQ ID NO 22
<211> LENGTH: 24
<212> TYPE: DNA
<213> ORGANISM: Artificial Sequence
<220> FEATURE:
<223> OTHER INFORMATION: oligonucleotide

<400> SEQUENCE: 22
gaggcgtaca gaaccactgc atag                                               24
```

HERBICIDE RESISTANT SORGHUM MUTANTS

CROSS-REFERENCE TO RELATED APPLICATIONS

This application claims benefit of priority from U.S. Provisional Application Ser. No. 61/490,114, filed on May 26, 2011, of which is incorporated herein by reference in its entirety.

TECHNICAL FIELD

This disclosure generally relates to sorghum mutants that exhibit herbicide resistance.

BACKGROUND

Sorghum (*Sorghum bicolor*) is a monocot in the Poaceae family. Sorghum has the ability to tolerate short-term drought, and a late summer sorghum crop may follow an early-season corn crop. Sorghum is being considered as an alternative grain crop for ethanol and feed, particularly in geographic areas that are more susceptible to dry soil conditions or where it is difficult to cultivate land early in the spring.

Weed control in sorghum is essential if high yields and efficient harvest are to be achieved; however, good weed control in sorghum fields is often difficult to achieve. Sorghum is a small seeded grass and is relatively slow growing in the first few weeks after emergence. In addition, sorghum will not tolerate many of the herbicides which can be effectively used on corn or other monocots. The slow seedling growth combined with the limited number of herbicides and the low rates that must be used makes weed control in sorghum difficult.

Thus, there is a need for sorghum plants that exhibit herbicide resistance.

SUMMARY

In one aspect, a first sorghum hybrid, variety, or line is provided. Such a hybrid, variety or line includes plants having a mutant acetolactate synthase (ALS), where the wild type ALS has the amino acid sequence shown in SEQ ID NO:2, and where the mutant ALS comprises the following amino acid substitutions: Ala-15-Gly, Pro-169-Leu, Arg-360-Gly, and Ile-532-Val, relative to SEQ ID NO:2. This mutant is referred to herein as Mutant A.

In another aspect, a second sorghum hybrid, variety, or line is provided. Such a hybrid, variety, or line includes plants having a mutant acetolactate synthase (ALS), where the wild type ALS has the amino acid sequence shown in SEQ ID NO:2, and where the mutant ALS comprises the following amino acid substitutions: Ala-15-Gly, Pro-169-Leu, and Ile-532-Val, relative to SEQ ID NO:2. This mutant is referred to herein as Mutant B.

In yet another aspect, a third sorghum hybrid, variety, or line is provided. Such a hybrid, variety, or line includes plants having a mutant acetolactate synthase (ALS), where the wild type ALS has the amino acid sequence shown in SEQ ID NO:2, and where the mutant ALS comprises the following amino acid substitutions: Ala-15-Gly, Ile-532-Val, and Trp-546-Leu, relative to SEQ ID NO:2. This mutant is referred to herein as Mutant C.

In yet another aspect, a fourth sorghum hybrid, variety, or line is provided. Such a hybrid, variety, or line includes plants having a mutant acetolactate synthase (ALS), where the wild type ALS has the amino acid sequence shown in SEQ ID NO:2, and where the mutant ALS comprises the following amino acid substitutions: Ala-15-Gly and Trp-546-Leu, relative to SEQ ID NO:2. This mutant is referred to herein as Mutant D.

Such hybrids, varieties, or lines typically are resistant to an ALS-inhibiting herbicide selected from the group consisting of sulfonylureas, imidazolinones, triazolopyrimides, and pyrimidinylthiobenzoates.

In still another aspect, a sorghum hybrid, variety, or line is provided. Such a hybrid, variety, or line includes plants having a mutant acetolactate synthase (ALS), where the sorghum hybrid, variety, or line is made by crossing plants from the sorghum hybrid, variety, or line referred to as Mutant A with plants from the sorghum hybrid, variety, or line referred to as Mutant B, C or D.

In still another aspect, a sorghum hybrid, variety, or line is provided. Such a hybrid, variety, or line includes plants having a mutant acetolactate synthase (ALS), where the sorghum hybrid, variety, or line is made by crossing plants from the sorghum hybrid, variety, or line referred to as Mutant B with plants from the sorghum hybrid, variety, or line referred to as Mutant C or D.

In still another aspect, a sorghum hybrid, variety, or line is provided. Such a hybrid, variety, or line includes plants having a mutant acetolactate synthase (ALS), where the sorghum hybrid, variety, or line is made by crossing plants from the sorghum hybrid, variety, or line referred to as Mutant C with plants from the sorghum hybrid, variety, or line referred to as Mutant D.

In one aspect, a method of making a sorghum hybrid, variety, or line is provided. Such a method typically includes the steps of: providing: a first sorghum plant having a mutant ALS, wherein the wild type ALS has the amino acid sequence shown in SEQ ID NO:2, wherein the mutant ALS comprises the following amino acid substitutions: Ala-15-Gly, Pro-169-Leu, Arg-360-Gly, and Ile-532-Val, relative to SEQ ID NO:2 (referred to herein as Mutant A); a second sorghum plant having a mutant ALS, wherein the wild type ALS has the amino acid sequence shown in SEQ ID NO:2, wherein the mutant ALS comprises the following amino acid substitutions: Ala-15-Gly, Pro-169-Leu, and Ile-532-Val, relative to SEQ ID NO:2 (referred to herein as Mutant B); a third sorghum plant having a mutant ALS, wherein the wild type ALS has the amino acid sequence shown in SEQ ID NO:2, wherein the mutant ALS comprises the following amino acid substitutions: Ala-15-Gly, Ile-532-Val, and Trp-546-Leu, relative to SEQ ID NO:2 (Mutant C); or a fourth sorghum plant having a mutant ALS, wherein the wild type ALS has the amino acid sequence shown in SEQ ID NO:2, wherein the mutant ALS comprises the following amino acid substitutions: Ala-15-Gly and Trp-546-Leu, relative to SEQ ID NO:2 (Mutant D); crossing the first or the second or the third or the fourth sorghum plant with a fifth sorghum plant that contains a desired phenotypic trait to produce one or more F1 progeny plants; collecting seed produced by the F1 progeny plants; and germinating the seed to produce sorghum plants comprising a mutant ALS, wherein the plants are resistant to inhibition by one or more ALS-inhibiting herbicides at levels that inhibit the growth of sorghum plants lacking the amino acid substitutions.

In certain embodiments, the desired phenotypic trait is selected from the group consisting of disease resistance, herbicide resistance, drought tolerance, high yield, seed quality, stalk size, early seed germination, sugar content in stalk, non-flowering and high total biomass yield. In certain embodiments, the first or the second or the third or the fourth sorghum plant also is resistant to inhibition by one or more herbicides other than ALS-inhibiting herbicides.

In another aspect, a purified mutant acetolactate synthase polypeptide is provided. Such a mutant ALS polypeptide imparts resistance to one or more ALS-inhibiting herbicides and that has the amino acid sequence shown in SEQ ID NO:4, SEQ ID NO:6, SEQ ID NO:8, and SEQ ID NO:10.

In another aspect, an isolated nucleic acid is provided. Such a nucleic acid encodes a mutant acetolactate synthase polypeptide that imparts resistance to one or more ALS-inhibiting herbicides and that has the nucleic acid sequence shown in SEQ ID NO:3, SEQ ID NO:5, SEQ ID NO:7, and SEQ ID NO:9.

In still another aspect, a transgenic sorghum plant cell is provided that includes a transformation vector. Generally, the transformation vector includes, in the 5' to 3' direction, regulatory elements that are functional in a sorghum plant cell operably linked to a mutant acetolactate synthase gene having the nucleic acid sequence shown in SEQ ID NO:3, SEQ ID NO:5, SEQ ID NO:7, or SEQ ID NO:9, where the transgenic plant cell is resistant to a level of one or more ALS-inhibiting herbicides that prevents or inhibits the growth of a wild type plant cell of the same species. In still another aspect, seed obtained from plants grown from such a transgenic sorghum plant cell is provided.

In yet another aspect, a method of controlling weeds in the vicinity of a sorghum plant is provided. In this aspect, the sorghum plant is from any of the hybrids, varieties, or lines described above (e.g., Mutant A, B, C, D, and crosses between/among Mutant A, B, C, and D). Such a method includes: a) providing one or more ALS-inhibiting herbicides, and b) applying the one or more ALS-inhibiting herbicides to one or more of the plants, where the growth of the weeds in the vicinity of the sorghum plant is adversely affected by the application of the one or more ALS-inhibiting herbicides while growth of the sorghum plant is not adversely affected. Representative classes of ALS-inhibiting herbicides include sulfonylureas, imidazolinones, triazolopyrimides, and pyrimidinylthiobenzoates.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DETAILED DESCRIPTION

Acetolactate synthase (ALS; EC 2.2.1.6) is the first common enzyme in the biosynthetic pathway of the branched-chain amino acids, valine, leucine, and isoleucine (Durner et al., 1990, *Plant Physiol.*, 93:1027-31). ALS requires thiamine diphosphate as a co-enzyme. In the biosynthesis of valine, two pyruvates are decarboxylated to 2-acetolactate and carbon dioxide; in the biosynthesis of isoleucine, the acetaldehyde from pyruvate is transferred to 2-oxobutanoate to form 2-aceto-2-hydroxybutanoate. The amino acid sequence of wild type sorghum ALS is shown in SEQ ID NO:2, and the nucleic acid sequence encoding the wild type sorghum ALS is shown in SEQ ID NO:1.

This disclosure describes the characterization of several shattercane mutants that were previously selected for resistance to various ALS-inhibiting herbicides (see, for example, Anderson et al., 1998, Weed Tech., 12:74-7; Anderson et al., 1998, Weed Sci., 46:158-62; and Lee et al., 1999, Weed Sci., 47:275-81). Shattercane is a subspecies of sorghum (*Sorghum bicolor* subsp. X *drummondii*) and, thus, traits from shattercane can be easily bred into sorghum to produce sorghum hybrids, varieties or lines. As used herein, "hybrid" refers to offspring or progeny of genetically dissimilar parent plants produced as the result of controlled cross-pollination; "variety" refers to a taxonomic nomenclature rank in botany, below subspecies, but above subvariety and form (see, also, the International Union for the Protection of New Varieties of Plants (UPOV) Convention definition of plant varieties); and "line" refers to a group of pure-breeding plants, distinguished from other individuals of the same species by a unique genotype and phenotype.

A first ALS mutant that imparts herbicide resistance to sorghum was determined to have the following amino acid substitutions (relative to SEQ ID NO:2): Ala-15-Gly, Pro-169-Leu, Arg-360-Gly, and Ile-532-Val. The amino acid sequence of this first mutant ALS is shown in SEQ ID NO:4, and the nucleic acid sequence encoding this first mutant ALS is shown in SEQ ID NO:3 (Appendix II). This mutant was designated Mutant A, and was determined to exhibit resistance to members of the Imizadolinone (e.g., Imazamox), Sulfonylurea (e.g., Chlorsulfuron, Foramsulfuron, and Primisulfuron) and Triazolone (e.g., Propoxycarbazone and Thiencarbazone) classes.

A second ALS mutant that imparts herbicide resistance to sorghum was determined to have the following amino acid substitutions (relative to SEQ ID NO:2): Ala-15-Gly, Pro-169-Leu, and Ile-532-Val. The amino acid sequence of this second mutant ALS is shown in SEQ ID NO:6, and the nucleic acid sequence encoding this second mutant ALS is shown in SEQ ID NO:5 (Appendix II). This mutant was designated Mutant B, and was determined to exhibit resistance to members of the Sulfonylurea (e.g., Chlorsulfuron, Foramsulfuron, and Primisulfuron) and Triazolone (e.g., Propoxycarbazone, and Thiencarbazone) classes.

A third ALS mutant that imparts herbicide resistance to sorghum was determined to have the following amino acid substitutions (relative to SEQ ID NO:2): Ala-15-Gly, Ile-532-Val, and Trp-546-Leu. The amino acid sequence of this third mutant ALS is shown in SEQ ID NO:8, and the nucleic acid sequence encoding this third mutant ALS is shown in SEQ ID NO:7 (Appendix II). This mutant was designated Mutant C, and was determined to exhibit resistance to members of the Imizadolinone (e.g., Imazamox, Imazaquin, and Imazethapyr), Pyrimidinyloxybenzoic acid (e.g., Bispyribac), Sulfonylurea (e.g., Chlorsulfuron, Foramsulfuron, Nicosulfuron, Primisulfuron, and Rimsulfuron), and Triazolone (e.g., Propoxycarbazone, and Thiencarbazone) classes.

A fourth ALS mutant that imparts herbicide resistance to sorghum was determined to have the following amino acid substitutions: Ala-15-Gly and Trp-546-Leu. The amino acid sequence of this fourth mutant ALS is shown in SEQ ID NO:10, and the nucleic acid sequence encoding this fourth mutant ALS is shown in SEQ ID NO:9 (Appendix II). This mutant was designated Mutant D. For the herbicides tested, this mutant was similar to wild type; however, given the mutations, may exhibit resistance to other herbicides.

Seeds from plants of the first, second, third and fourth mutants described herein were deposited with American Type Culture Collection (ATCC) on May 23, 2011 under Accession Nos. PTA-11896, PTA-11897, PTA-11898, and PTA-11899, respectively.

As used herein, the term "mutant ALS" refers to ALS nucleic acid and/or polypeptide sequences that differ from the corresponding wild type sequence(s). The particular mutations in the sorghum plants described herein are substitutions of one amino acid for another, although other types of mutations at or around or including the positions described herein also can result in resistance to ALS-inhibiting herbicides. In addition to amino acid substitutions (e.g., a point mutation in the nucleic acid resulting in a conservative substitution, a non-conservative substitution, or a stop codon), other types of mutations include, for example, insertions, deletions, and inversions.

As used herein, a "functional mutant" refers to a protein or polypeptide that has a different sequence from the wild type sequence but still retains enzymatic activity or, at least, partial enzymatic activity. In the present application, a mutant ALS typically refers to a functional mutant, in that the mutant ALS polypeptide retains at least some of its activity to synthesize essential amino acids, even in the presence of a chemical that inhibits the wild type ALS enzymatic activity. Thus, such a mutant ALS polypeptide is resistant to the ALS-inhibiting herbicide and is said to impart or confer herbicide resistance to the mutant plant.

As would be known to those skilled in the art, there is degeneracy in the genetic code. That is, there are many instances in which different codons specify the same amino acid; or, in other words, some amino acids may each be encoded by more than one codon. Therefore, the nucleic acid sequences that encode the mutant ALS polypeptides described herein can vary in sequence, and SEQ ID NOs: 3, 5, 7 and 9 are representative nucleic acid sequences that encode the mutant ALS polypeptides having the amino acid sequences shown in SEQ ID NOs: 4, 6, 8 and 10. In addition to differences in sequence due to the degeneracy of the genetic code, mutant ALS nucleic acids and polypeptides as described herein may have a sequence that differs from the wild type sequences, notwithstanding the positions identified herein containing mutations. For example, a mutant ALS nucleic acid or polypeptide can have a nucleic acid sequence or amino acid sequence that has at least 70% sequence identity (e.g., at least 80%, at least 85%, at least 90%, at least 95%, at least 96%, at least 97%, at least 98%, or at least 99%) to wild type ALS (SEQ ID NO:1 or 2, respectively).

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It will be appreciated that a single sequence can align differently with other sequences and hence, can have different percent sequence identity values over each aligned region. It is noted that the percent identity value is usually rounded to the nearest integer. It is also noted that the length of the aligned region is always an integer.

The alignment of two or more sequences to determine percent sequence identity is performed using the algorithm described by Altschul et al. (1997, Nucleic Acids Res., 25:3389-3402) as incorporated into BLAST (basic local alignment search tool) programs, available at ncbi.nlm.nih.gov on the World Wide Web. BLAST alignments using the Altschul et al. algorithm can be performed to determine percent sequence identity between one sequence and any other sequence or portion thereof. BLASTN is the program used to align and compare the percent sequence identity between nucleic acid sequences, while BLASTP is the program used to align and compare the percent sequence identity between amino acid sequences. When utilizing BLAST programs to calculate the percent identity between a sequence of the invention and another sequence, the default parameters of the respective programs are used.

In addition, fragments of mutant ALS polypeptides having the amino acid sequences shown in SEQ ID NOs: 4, 6, 8 and 10 are described herein. As used herein, the term "fragment" refers to portions of a protein, while the term "functional fragment" refers to portions of a protein that retain at least partial functional activity. A fragment may be as small as four amino acid residues (e.g., for use as an immunogen) or as large as the entire amino sequence less one amino acid or more.

Breeding of Sorghum Plants

Sorghum plants are, by nature, self-pollinating plants, but they can be bred by cross-pollination. Sleper and Poehlman (2006, *Breeding Field Crops*, Fifth Ed., Wiley-Blackwell Publishing) provides a review of current breeding procedures for field crops including sorghum.

Breeding typically starts with the crossing of two genotypes. As indicated herein, initial crosses may be performed between any one of the four ALS mutants described herein and any other of the four ALS mutants described herein. For example, in certain embodiments, the first ALS mutant described herein can be crossed with the second ALS mutant, the third ALS mutant, or the fourth ALS mutant described herein. In some embodiments, the second ALS mutant described herein can be crossed with the third ALS mutant or the fourth ALS mutant described herein; and, in other embodiments, the third ALS mutant described herein can be crossed with the fourth ALS mutant. Unless specifically indicated otherwise, the references herein to crossing one group of plants with another group of plants is not meant to be interpreted to limit either group to male or female plants. That is, a cross between, for example, a first ALS mutant plant described herein and a second ALS mutant plant described herein refers to crosses where the first ALS mutant plants are males and to crosses where the first ALS mutant plants are females.

In some cases, other plants (e.g., fifth plants) having desired traits can be included in a breeding population. For example, if plants are desired that exhibit ALS-inhibiting herbicide resistance as described herein and resistance to another herbicide, then plants having each attribute can be crossed using classical plant breeding techniques. In another example, plants exhibiting ALS-inhibiting herbicide resistance can be crossed with plants having a desired phenotypic trait such as, but not limited to, disease resistance, drought tolerance, high yield, seed quality, stalk size, early seed germination, sugar content in stalk, non-flowering high total biomass yield, and herbicide resistance. Certain plants having a desired phenotypic trait may be referred to as "elite plants," which typically are plants that resulted from breeding and selection for superior agronomic performance. Representative elite sorghum lines include, but are not limited to, Tx430, Tx2737, Tx2783, 00MN7645, HP162, Wheatland, Tx3042, OK11, QL41 and Tx643.

As used herein, "filial generations" refer to the consecutive generations of plants after a bi-parental cross (i.e. a cross between two genetically different parents). The generation resulting from a bi-parental cross is the first filial generation (i.e., "F1"), with respect to the seed and the corresponding plants, while the generation resulting from a cross between F1 plants is the second filial generation (i.e., "F2"), with respect to the seed and the corresponding plants. Plants (e.g., F1 plants, F2 plants, etc.) can be selfed for any number of generations (e.g., S1, S2, S3, etc.) or backcrossed for any number of generations (e.g., BC1, BC2, BC3, etc.). Combinations of bi-parental crosses, selfing, and backcrossing are used by plant breeders to move one or more traits from one line or variety into another, to stabilize such traits in the line or variety, and, in certain instances, to make the plants in the line or variety homozygous for the trait. Such well known breeding methods can be used to produce plants having the desired traits.

Hybrid development is well known in the art. In current hybrid sorghum breeding programs, new parent lines are developed to be either seed-parent lines or pollen-parent lines, depending on whether or not they contain fertility-restoring genes. That is, the seed-parent lines do not have fertility restoring genes and are male-sterile in certain cytoplasm (also known as "A-line" plants) and male fertile in other cytoplasm (also known as "B-line" plants), whereas the pollen-parent lines are not male sterile and do contain fertility restoring genes (also known as "R-line" plants). The seed-parent lines can be cytoplasmically male sterile such that the anthers are minimal to non-existent in these plants or they can be bred to contain genetically recessive male-sterile nuclear genes. The seed-parent lines will only produce seed, and the cytoplasm is transmitted only through the egg. The pollen for cross-pollination is furnished by the pollen-parent, which contains the genes necessary for complete fertility restoration in the F1 hybrid. Typically, hybrid seed is produced by planting blocks of rows of male sterile (seed-parent) plants and blocks of rows of fertility restorer (pollen-parent) plants, such that the seed-parent plants are wind pollinated with pollen from the pollen-parent plants. This process results in the production of hybrid plants.

Transgenic Plants and Methods of Making

Nucleic acids encoding mutant ALS enzymes that are intended for expression in plants are first assembled in transformation vectors containing the mutant ALS nucleic acid operably linked to the appropriate regulatory elements. Regulatory elements are required for expression in a plant and include, without limitation, promoters, enhancers (e.g., introns), transcriptional terminator sequences, polyadenylation signals, localization signals (e.g., a nuclear localization signal (Kalderon et al., 1984, *Cell,* 39:499; Lassner et al., 1991, *Plant Mol. Biol.,* 17:229)).

Promoters, for example, can be categorized as constitutive promoters, tissue-, organ-, or developmentally-specific promoters, and inducible promoters. Representative promoters that are known to function in plants include, but are not limited to, the 35S promoter of cauliflower mosaic virus (CMV); leucine amino peptidase from tomato (Chao et al., 1999, *Plant Physiol.,* 120:979-992); Pathogenesis-Related (PR)-1 from tobacco; heat shock promoters (e.g., U.S. Pat. No. 5,187,267); tetracycline-inducible promoter (U.S. Pat. No. 5,057,422); and numerous seed-specific promoters. Terminators, for example, are responsible for the termination of transcription and the correct polyadenylation of the transcript. Representative transcriptional terminators that are known to function in plants include, but are not limited to, the CaMV 35S terminator, the tml terminator, the pea rbcS E9 terminator, and the nopaline and octopine synthase terminator. See, for example, Odell et al., 1985, *Nature,* 313:810; Rosenberg et al., 1987, *Gene,* 56:125; Guerineau et al., 1991, *Mol. Gen. Genet.,* 262:141; Proudfoot, 1991, *Cell,* 64:671; Sanfacon et al., 1990, *Genes Dev.,* 5:141; Mogen et al., 1990, *Plant Cell,* 2:1261; Munroe et al., 1990, *Gene,* 91:151; Ballas et al., 1989, *Nucleic Acids Res.,* 17:7891; Joshi et al., 1987, *Nucleic Acid Res.,* 15:9627.

Typically, transformation vectors also will include an antibiotic or herbicide selection marker. Selection markers used routinely in plant transformations include the nptII gene, which confers resistance to kanamycin (Messing & Vierra, 1982, *Gene,* 19: 259; Bevan et al., 1983, *Nature,* 304:184), the bar gene, which confers resistance to the herbicide, phosphinothricin (White et al., 1990, *Nucl Acids Res.,* 18:1062; Spencer et al., 1990, *Theor. Appl. Genet.,* 79:625), the hph gene, which confers resistance to the antibiotic hygromycin (Blochlinger & Diggelmann, 1984, *Mol. Cell. Biol.,* 4:2929), and the dhfr gene, which confers resistance to methotrexate (Bourouis et al., 1983, *EMBO J.,* 2:1099).

Methods of making transformation vectors are well known to those skilled in the art. Methods include recombinant DNA techniques, in vitro mutagenesis, synthetic techniques, and in vivo genetic recombination. Exemplary techniques are widely described in the art (see, e.g., Sambrook. et al., 1989, *Molecular Cloning, A Laboratory Manual,* Cold Spring Harbor Press, Plainview, N.Y., and Ausubel, et al., 1989, *Current Protocols in Molecular Biology,* John Wiley & Sons, New York, N.Y.). A nucleic acid sequence within a transformation vector can be manipulated so as to provide for the sequences in the desired orientation (e.g., sense or antisense) or reading frame.

Numerous transformation vectors are available for plant transformation, and the selection of a vector will depend upon the preferred transformation technique and the target species for transformation. In some embodiments, a Ti plasmid vector (T-DNA) is used in an *Agrobacterium* mediated transformation process (e.g., U.S. Pat. Nos. 6,369,298, 6,051,757, 5,981,840, 5,981,839, 5,824,877 and 4,940,838; and Herrera-Estrella, 1983, *Nature,* 303:209-13; Fraley et al., 1983, *Proc. Natl. Acad. Sci,* USA, 80:4803-7; Horsch et al., 1984, *Science,* 223:496-8; and DeBlock et al., 1984, *EMBO J.,* 3:1681-9). *Agrobacterium* mediated transformation can utilize a single vector ("co-integration"), where the vector contains both the cis-acting and trans-acting elements required for plant transformation, or two vectors (a "binary" vector system), where the transgene is inserted into a vector containing the cis-acting elements required for plant transformation and a second vector contains the trans-acting elements. Representative co-integration vectors include, for example, pMLJ1 and Ti plasmid pGV3850, while representative binary vector systems include, for example, the pBIN19 shuttle vector and the non-oncogenic Ti plasmid PAL4404.

In addition to *Agrobacterium* mediated introduction of nucleic acids, a transformation vector can be introduced into plant cells using any number of art-recognized methods. For example, in one embodiment, a transformation vector can be microinjected directly into plant cells (Crossway, 1985, *Mol. Gen. Genet.,* 202:179). In certain embodiments, a transformation vector is introduced into a plant cell using polyethylene glycol (Krens et al., 1982, *Nature,* 296:72; Crossway et al., 1986, *BioTechniques,* 4:320); protoplasts fusion (Fraley et al., 1982, *Proc. Natl. Acad. Sci. USA,* 79:1859); protoplast transformation (EP 0 292 435); or direct gene transfer (Paszkowski et al., 1984, *EMBO J.,* 3:2717; Hayashimoto et al., 1990, *Plant Physiol.,* 93:857). In some embodiments, a transformation vector can be introduced into plant cells by electroporation (Fromm et al., 1985, *Proc. Natl. Acad. Sci. USA,* 82:5824; Riggs et al., 1986, *Proc. Natl. Acad. Sci. USA,* 83:5602). In some embodiments, a transformation vector can be introduced through ballistic particle acceleration or particle bombardment (U.S. Pat. No. 4,945,050; Casas et al., 1993, *Proc. Natl. Acad. Sci. USA*, 90:11212).

In some embodiments, the nucleic acid sequence of interest is targeted to a particular locus within the plant genome. Site-directed integration of the nucleic acid sequence of interest into the plant genome may be achieved using, for example, homologous recombination. For example, plant cells can be incubated with *Agrobacterium* that contains a transformation vector in which sequences that are homologous to sequences within the target locus are flanked by the *Agrobacterium* T-DNA sequences (see, for example, U.S. Pat. No. 5,501,967).

After selecting for transformed plant cells that express a mutant ALS imparting herbicide resistance, whole plants are regenerated. Plant regeneration from cultured protoplasts is described in Evans et al., *Handbook of Plant Cell Cultures*, Vol. 1, MacMillan Publishing Co. New York, (1983); and Vasil I. R. (ed.), *Cell Culture and Somatic Cell Genetics of Plants*, Acad. Press, Orlando, Vol. I, (1984) and Vol. III, (1986). Means for regeneration of plants vary from species to species. In one embodiment, callus tissue can be formed, following induction of shoots and subsequent rooting. Alternatively, embryo formation can be induced, which ultimately germinate and form mature plants. The culture media used for regenerating plants typically contains amino acids and hormones such as auxins and cytokines.

Mutagenesis of Sorghum

The ALS mutants described herein also can be obtained by inducing mutagenesis in plant cells or tissue. For example, sorghum cells or seeds can be mutagenized with one or more commonly-used mutagens. Mutagens can be chemical mutagens (e.g., nitrous acid, sodium azide, acridine orange, ethidium bromide, and ethyl methane sulfonate) or ionizing radiation mutagens (e.g., X-rays, gamma rays, and UV radiation). Mutagenesis also can utilize transposons or T-DNA insertional mutagenesis. In another embodiment, sorghum cells or tissue can be cultured to induce somaclonal variants. For example, protoplasts can be cultured to produce callus tissue, which then can be regenerated into plants using well known tissue culture methods.

The mutagenized population (i.e., M0), or a subsequent generation of that population (i.e., M1, M2, M3, etc.), then can be screened for the desired trait (e.g., resistance to an ALS-inhibiting herbicide) that results from the mutation(s). Alternatively or additionally, the mutagenized population, or a subsequent generation of that population, is screened directly for a mutation of interest (e.g., by sequencing the ALS gene or a portion thereof). As discussed herein, the particular herbicide resistance has been identified for Mutants A, B and C, and crosses between and among any of the mutants disclosed herein (i.e., Mutant A, B, C and D) for one or more generations can result in progeny having any number of different combinations of the following amino acid substitutions: Ala-15-Gly, Pro-169-Leu, Arg-360-Gly, Ile-532-Val, or Trp-546-Leu.

Methods of Weed Control

For sorghum to be an economically sustainable field crop, growth of grassy weeds must be controlled. There are fewer options for weed control in sorghum than in corn, cotton and soybeans. Sorghum lacks tolerance to many of the commonly used grass and broadleaf herbicides, and is occasionally injured even by herbicides labeled for use with sorghum. The hybrids, varieties and lines described herein, or progeny of those plants or progeny of crosses with those plants, allow for weed control. Plants from these hybrids, varieties or lines, or progeny thereof, can be grown in fields onto which one or more ALS-inhibiting herbicides can be applied, without adversely affecting the growth of the sorghum plants, while inhibiting or adversely affecting the growth of the weeds in the field. The most troublesome weeds for grain sorghum include morning glory, pigweed, broadleaf signal grass, barnyard grass, prickly sida (or teaweed), crabgrass and sicklepod.

The mutant ALS sorghum plants described herein exhibit resistance against one or more of the ALS-inhibiting classes of herbicides as indicated above. As used herein, "ALS-inhibiting herbicide" refers to any member of a group of herbicides that inhibit the activity of acetolactate synthase in a plant. Since ALS is also known as acetohydroxyacid synthase, ALS-inhibiting herbicides are sometimes referred to as "AHAS herbicides." ALS-inhibiting herbicides fall into five structurally different classes of chemicals (see, for example, Corbett et al., 2006, *Pest Manag. Sci.*, 62:584-97). Such classes, and representative members of each class, include:

sulfonylureas (SUs) such as, without limitation, amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flupyrsulfuron-methyl-sodium, foramsulfuron, halosulfuron-methyl, imazolsulfuron, iodosulfuron-methyl-sodium, mesosulfuron-methyl, metsulfuron-methyl, nicosulfuron, oxasulfuron, primisulfuron-methyl, pyraxosulfuron-ethyl, rimsulfuron, sulfometuron-methyl, sulfosulfuron, thifensulfuron-methyl, triasulfuron, tribenuron-methyl, trifloxysulfuron-sodium, triflusulfuron-methyl, triofensulfuron, and tritosulfuron. See, for example, Chaleff and Mauvais, 1984, *Science*, 224:1443-5.

imidazolinones (IMIs) such as, without limitation, imazamethabenz-methyl, imazamox, imazapic, imizapyr, imizaquin, and imazethapyr. See, for example, Shaner et al., 1984, *Plant Physiol.*, 76:545-6.

pyrimidinylthiobenzoates (PTBs) such as, without limitation, bispyribac-sodium, pyribenzoxim, pyriftalid, pyriminobac-methyl, and pyrithiobac-sodium. See, for example, Stidham, 1991, *Weed Sci.*, 39:428-34.

triazolopyrimidine sulfonanilides (TPs) such as, without limitation, cloransulam-methyl, diclusolam, florasulam, flumetsulam, metosulam, and penoxsulam. See, for example, Gerwick et al., 1990, *Pestic. Sci.*, 29:357-64.

sulfonylamino carbonyl triazolinones (SCTs) such as, without limitation, thiencarbazone-methly, flucarbazone, propoxycarbazone. See, for example, U.S. Pat. Nos. 6,395,684 and 6,403,535.

Without being bound by any particular mechanism, resistance to ALS-inhibiting herbicides can result from an altered ALS enzyme with reduced sensitivity to the herbicides (Saari et al., 1994, "Resistance to acetolactatesynthase inhibiting herbicides," pp 83-139, Eds. Powles and Holtum, *Herbicide Resistance in Plants: Biology and Biochemistry*, CRC, Boca Raton, Fla.), and resistance can be conferred by a single amino acid substitution (Shaner, 1999, *Weed Sci.*, 44:405-11). However, resistance to ALS-inhibiting herbicides also can result from enhanced rates of herbicide metabolism (Christopher et al., 1991, *Plant Physiol.*, 95:1036-43; Christopher et al., 1992, *Plant Physiol.*, 100:1909-13; Menendez et al., 1997, *Physiologia Plantarum*, 99:97-104; and Veldhuis et al., 2000, J. Agric. Food Chem., 48:2986-90).

In some embodiments, the ALS-inhibiting herbicide comprises a combination of active ingredients from one or more of the classes disclosed herein. However, the present application is not limited to existing commercially available ALS-inhibiting herbicides, and a skilled artisan will appreciate that new chemicals may be identified that inhibit the ALS enzyme.

In certain instances, it may be desirable to produce sorghum plants that, in addition to the mutations described herein that impart resistance to ALS-inhibiting herbicides, further exhibit resistance to a herbicide from another group. For example, other herbicide groups (i.e., non-ALS-inhibiting herbicides) used to inhibit weed growth include, without limitation, inhibitors of lipid synthesis (e.g., benzofuranes, chlorocarbonic acids, cyclohexanodeiones, thiocarbamates), inhibitors of photosynthesis at photosystem I (e.g., bipyridyliums), inhibitors of photosynthesis at photosystem II (e.g., phenylcarbamates, pyridazinones, triazines, triazinones, triazolinones, uracils, amides, ureas, benzothiadiazinones, nitriles, phenyl-pyridines), inhibitors of carotenoid biosynthesis (e.g., pyridazinones, pyridinecarboxamides, isoxazolidinones, triazoles), inhibitors of protoporphyrinogen oxidase (e.g., diphenylethers, N-phenylphthalimides, oxadiazoles, oxyzolidinediones, phenylpyrazoles, pyrimidindiones, thiadiazoles), inhibitors of 4-hydroxyphenyl-pyruvate-dioxygenase (e.g., callistemones, isoxazoles, pyrazoles, triketones), inhibitors of EPSP synthase (e.g., glycines), inhibitors of glutamine synthetase (e.g., phosphinic acids), inhibitors of dihydropteroate synthase (e.g., carbamates), inhibitors of microtubule assembly (e.g., benzamides, benzoic acids, dinitroanilines, phosphoroamidates, pyridines), inhibitors of cell division (e.g., acetamides, chloroacetamides, oxyacetamides), inhibitors of cell wall synthesis (e.g., nitriles, triazolocarboxamides) and inhibitors of auxin transport (e.g., phthalamates, semicarbazones). Such plants can be produced using known methods (e.g., breeding or transgenic methods as described herein).

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1

Plant Materials

Shattercane seed was initially collected in 1991 from fields previously treated with primisulfuron for either 2 or 3 years. A second collection was made in 1992 from the same fields that had again been treated with primisulfuron. All seed was evaluated under greenhouse conditions with IX (40 g ai/ha) and 0.25× rates of primisulfuron. Plants surviving the IX treatment were treated a second time with a 2× application. This screening process resulted in the discovery of four plants resistant to both the IX and 2× applications.

Example 2

Assay for Resistance

The bioassay experiment was conducted in a greenhouse on the East Campus of the University of Nebraska-Lincoln, in Lincoln, Nebr. The experimental design was a randomized complete block. Shattercane seed was planted in 0.9 L square plastic pots in Miracle-Gro® Moisture Control® Potting Mix (The Scotts Company LLC, Marysville, Ohio). The photoperiod was 15/9 light/dark with supplemental light provided by sodium halide lamps. Greenhouse temperatures were maintained at 24±2 C (day) and 19±2 C (night). Shattercane was thinned to 1 plant per pot when it reached the 2 leaf stage. Herbicide treatments (Table 1 in Appendix I) were applied when the shattercane reached the V4 growth stage and was approximately 12 cm tall. Individual plants ranged from growth stage V3 to V5, and in height from 7 to 19 cm. At least one tiller had formed on most plants by the time of application. Herbicides were applied using an 8001 even flat fan nozzle at 207 kPa in a single-tip track sprayer located in the greenhouse facility. The application rate was 187 l/ha, and treatment solutions were prepared in distilled water. Visual injury ratings were made 7, 14 and 21 days after treatment on a scale of 0 to 100, where 0 represents no injury and 100 represents plant death. At 21 DAT, plants were harvested at the soil surface, dried for 48 h at 70 C, and weighed to determine dry matter. Dry matter data for each experimental unit was divided by the average dry matter of the untreated control plants of that biotype and multiplied by 100 to determine relative percent biomass to the untreated control. Dry matter data for each experimental unit was also divided by the average dry matter data of the glyphosate-treated plants of that biotype to determine growth in the three weeks after herbicide application. Data were subjected to ANOVA using Proc GLM of SAS 9.1 (SAS Institute Inc., Cary, N.C.). The Run by Herbicide by Population interaction was significant for each variable, so runs were analyzed separately. The Herbicide by Population interaction was also significant for each run and each variable, so data were analyzed by herbicide to describe differences among the populations. Treatment means were separated using Duncan's Multiple Range test.

Example 3

ALS Gene Sequencing

Genomic DNA Extraction

Leaves from the plants and biotypes used for the ALS activity assay were individually sampled at the four-leaf stage for DNA extraction. Genomic DNA was extracted from leaf tissue of five plants per biotype using the CTAB (cetyltrimethyl ammonium bromide) DNA protocol (Doyle et al., 1987, *Phytochem. Bull.*, 19:11-5).

ALS Gene Isolation:

The primers were designed from previously published corn ALS sequence region (Feng et al., 1992, *Plant Mol. Biol.*, 18:1185-7). Phusion® DNA polymerase (New England BioLabs) was used to amplify the ALS gene fragments from genomic DNA of four mutants and wild type in separate PCR reactions. The PCR cocktail consisted of genomic DNA, 4 µl (25 ng/µl concentration); forward and reverse primer, 2 µl each (20 pmol); 10 mM dNTP's, 2.5 µl; 100% DMSO, 2 µl; 5× Phusion® GC reaction buffer, 10 µl; Phusion DNA polymerase, 1 µl (2 units); and water, 21.5 µl; to bring the final volume to 50 µl. The PCR reaction protocol consisted of 30 sec of incubation at 98° C., followed by 35 cycles at 98° C. for 15 sec, annealing at X° C. for 30 sec and 72° C. for 15 sec; then a final extension at 72° C. for 7 minutes, where X is the annealing temperature for each primer set used (Table 5 in Appendix I).

The PCR amplified products were resolved on a 1% (wt/v) agarose gel containing 1 µl ethidium bromide at 10 mg/ml. The desired PCR fragments were excised from the gel and purified using Qiagen Gel Extraction Kit, and the purified fragments of different sizes were directly sequenced using an automated sequencer, and the primers used for sequencing were the same as those used for PCR amplification. Each PCR product was sequenced in both forward and reverse directions to minimize sequencing errors. The generated nucleotide sequences from each sample were aligned with Bioedit sequence alignment editor software. The aligned sequences were compared with the sorghum ALS gene sequence by Pairwise alignment to check the coverage of the gene by each primer. After alignment, the overlapped regions from the fragments were removed and the fragments were joined to make a contiguous and full-length sequence from each sample. Completely aligned sequences of the four mutants were compared with the wild type sequence using ClustaW (ClustalW Multiple alignment tool, European Bioinformatics Institute, ebi.ac.uk/clustalW/ on the World Wide Web) to detect single nucleotide changes. The nucleotide sequence from each mutant and wild type was translated into the amino acid sequence. The amino acid sequence of mutants was compared with both wild type sequences in sorghum and the susceptible shattercane wild type to identify the amino acid substitutions using ClustalW.

Example 4

Pyramiding of ALS Genes

The four genes that confer resistance to ALS-inhibiting herbicides in shattercane were introgressed into three elite inbred lines of sorghum, N250, N252, and N532, for the purpose of developing and deploying herbicide-resistant inbreds and hybrids. ALS-inhibiting herbicide resistance was transferred to sorghum by crossing sorghum with shattercane. Crosses were developed in a greenhouse as follows: all sorghum lines were used as females and the three inbreds contained nuclear male sterility genes to eliminate the need for emasculation and to reduce the probability of selfing. The inbred sorghum lines, N 250 ms1, N252 ms3 and N532 ms7, were crossed manually with the four shattercane resistant plants. The F1 hybrids are backcrossed several generations to remove the genetic drag associated with shattercane, using the same female plant. The BC1 and BC2 generations are screened for resistance using herbicides representing the four classes of ALS-inhibiting herbicides. Panicles from the surviving BC2 plants are bagged and allowed to self-pollinate for several generations. To extend the durability of resistance, the ALS genes are stacked in all combinations to produce sorghum lines that contain one, two, three or four mutant ALS genes.
  Cross #1: N250 ms1×P2-2-05
  Cross #2: N250 ms1×P8-30
  Cross #3: N250 ms1×P9-102
  Cross #4: N250 ms1×5-4FARM
    To Pyrimid Two Genes
  Cross #5: Cross #1×Cross #2
  Cross #6: Cross #1×Cross #3
  Cross #7: Cross #1×Cross #4
  Cross #8: Cross #2×Cross #3
  Cross #9: Cross #2×Cross #4
  Cross #10: Cross #3×Cross #4
    To Pyrimid Three Genes
  Cross #5×Cross #3 (to pyramid 1, 2, and 3)
  Cross #5×Cross #4 (to pyramid 1, 2, and 4)
  Cross #2×Cross #10 (to pyramid 2, 3, and 4)
  Cross #1×Cross #10 (to pyramid 1, 3, and 4)
    To Pyramid Four Genes
  Cross #5×Cross #10 (to pyramid 1, 2, 3, and 4)
The same crossing scheme is used to pyramid the ALS gene into N252 ms3 and N532 ms7.

Example 4

Experimental Results

Resistance to ALS-inhibiting herbicides varied by biotype. The wild type and biotype 5-4Farm responded to the herbicides similarly (Table 2 in Appendix I). The only herbicide that did not reduce dry matter of these two biotypes was penoxsulam. Penoxsulam is from the triazolopyrimidine class. Herbicides from this class have limited activity on grass species. Penoxsulam was selected to represent this chemical family because it controls some grass weeds (*Echinochloa* species).

Biotype P8-30 showed resistance relative to the wild-type to all ALS-inhibiting herbicides tested (Table 2 in Appendix I). For two herbicides, bispyribac and rimsulfuron, only partial resistance was observed, and growth was reduced approximately 65% and 84%, respectively. Biotype P9-102 was resistant to foramsulfuron, nicosulfuron, and propoxycarbazone (Table 2 in Appendix I), and was partially resistant to primisulfuron and thiencarbazone (Table 3 in Appendix I). Biotype P2-205 was resistant to chlorsulfuron and propoxycarbazone (Table 2 in Appendix I) and partially resistant to imazamox, foramsulfuron, primisulfuron, and thiencarbazone (Table 3 in Appendix I). Visual ratings allowed distinction between plants that were severely stunted but still capable of completing their life cycle and plants that were severely stunted and near death. It was on this basis that these "partial resistance" labels was suggested.

A total of 2170 by ALS gene from sorghum CK60, shattercane, and four mutants were sequenced. Mutant's gene sequence is highly conserved with wild type with few amino acid changes. In comparison with the wild type sequence, a nucleotide change of GCC to GGC at position 45, relative to SEQ ID NO:1, was observed in all four mutants (P2-2-05, P8-30, P9-102 and 5-4FARM) and coded for an Ala to Gly substitution at residue 15 ($Ala_{15}$ Gly), relative to SEQ ID NO:2. In addition, a nucleotide change of CCG to CTG at position 507, relative to SEQ ID NO:1, was observed in two mutants, P2-2-205 and P9-102, and coded for a $Pro_{169}$ Leu substitution, relative to SEQ ID NO:2. A nucleotide change of AGG to GGG at position 1079, relative to SEQ ID NO:1, was observed in mutant P2-2-205 and coded for a $Arg_{360}$ Gly substitution, relative to SEQ ID NO:2. A nucleotide change of ATC to GTC at position 1595, relative to SEQ ID NO:1 was observed in three mutants, P2-2-205, P8-30 and P9-102, which coded for a $Ile_{532}$ Val substitution, relative to SEQ ID NO:2. A nucleotide change of TGG to TTG at position 1638, relative to SEQ ID NO:1, was observed in two mutants, P8-30 and 5-4farm, and coded for a $Trp_{546}$ Leu substitution, relative to SEQ ID NO:2. These changes are summarized in Table 4 in Appendix I.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A sorghum plant comprising a mutant acetolactate synthase (ALS), wherein the wild type ALS has the amino acid sequence shown in SEQ ID NO:2, wherein said mutant ALS comprises the following amino acid substitutions: Ala-15-Gly, Pro-169-Leu, Arg-360-Gly, and Ile-532-Val, relative to SEQ ID NO:2.

2. The sorghum plant of claim 1, wherein said plant has a mutant ALS exhibit resistance to one or more ALS-inhibiting herbicides selected from the group consisting of sulfonylureas, imidazolinones, triazolopyrimides, and pyrimidinylthiobenzoates.

3. A method of making a sorghum plant, comprising the steps of:
   providing:
   a first sorghum plant having a mutant ALS, wherein the wild type ALS has the amino acid sequence shown in SEQ ID NO:2, wherein said mutant ALS comprises the following amino acid substitutions: Ala-15-Gy, Pro-169-Leu, Arg-360-Gy, and Ile-532-Val, relative to SEQ ID NO: 2;
   crossing said first sorghum plant with a second sorghum plant that contains a desired phenotypic trait to produce one or more F1 progeny plants;
   collecting seed produced by said F1 progeny plants; and
   germinating said seed and selecting for the mutant ALS to produce sorghum plants comprising a mutant ALS, wherein said plants are resistant to inhibition by one or more ALS-inhibiting herbicides at levels that inhibit the growth of sorghum plants lacking said amino acid substitutions.

4. The method of claim 3, wherein said desired phenotypic trait is selected from the group consisting of disease resistance, herbicide resistance, drought tolerance, high yield, seed quality, stalk size, early seed germination, sugar content in stalk, non-flowering and high total biomass yield.

5. The method of claim 3, wherein said first or said second sorghum plant further comprises resistance to inhibition by one or more herbicides other than ALS-inhibiting herbicides.

6. A method of controlling weeds in the vicinity of a sorghum plant, wherein said sorghum plant is the sorghum plant of claim 1, comprising:
   a) providing one or more ALS-inhibiting herbicides, and
   b) applying said one or more ALS-inhibiting herbicides to one or more of said plants,
   wherein the growth of said weeds in the vicinity of said sorghum plant is adversely affected by the application of said one or more ALS-inhibiting herbicides while growth of said sorghum plant is not adversely affected.

7. The method of claim 6, wherein said one or more ALS-inhibiting herbicides are selected from the group consisting of sulfonylureas, imidazolinones, triazolopyrimides, and pyrimidinylthiobenzoates.

* * * * *

UNITED STATES PATENT AND TRADEMARK OFFICE
CERTIFICATE OF CORRECTION

PATENT NO.         : 9,365,862 B1                                            Page 1 of 1
APPLICATION NO.    : 13/480576
DATED              : June 14, 2016
INVENTOR(S)        : Ismail M. Dweikat It is certified that error appears in the above-identified patent and that said Letters Patent is hereby corrected as shown below:

Claims

Column 45, Line 43 (approx.), In claim 3, delete "Gy" and insert -- Gly --, therefor.

Column 45, Line 44 (approx.), In claim 3, delete "Gy" and insert -- Gly --, therefor.

Signed and Sealed this
Twenty-third Day of August, 2016

Michelle K. Lee
*Director of the United States Patent and Trademark Office*